(12) United States Patent
Asaad et al.

(10) Patent No.: US 9,034,022 B2
(45) Date of Patent: May 19, 2015

(54) LOCKING FORCE AUGMENTATION FEATURES FOR SURGICAL SCREW ASSEMBLY

(71) Applicants: Wagdy W. Asaad, Burr Ridge, IL (US); Jayson Varghese, Niles, IL (US)

(72) Inventors: Wagdy W. Asaad, Burr Ridge, IL (US); Jayson Varghese, Niles, IL (US)

(73) Assignee: SpineCraft, LLC, Westmont, IL (US)

(*) Notice: Subject to any disclaimer, the term of this patent is extended or adjusted under 35 U.S.C. 154(b) by 410 days.

(21) Appl. No.: 13/717,565

(22) Filed: Dec. 17, 2012

(65) Prior Publication Data

US 2014/0046385 A1 Feb. 13, 2014

Related U.S. Application Data

(63) Continuation-in-part of application No. 13/570,374, filed on Aug. 9, 2012.

(51) Int. Cl.
*A61B 17/88* (2006.01)
*A61B 17/86* (2006.01)
*A61B 17/70* (2006.01)
*A61B 19/00* (2006.01)

(52) U.S. Cl.
CPC .............. *A61B 17/88* (2013.01); *A61B 17/8605* (2013.01); *A61B 17/7032* (2013.01); *A61B 17/7034* (2013.01); *A61B 17/7035* (2013.01); *A61B 17/7038* (2013.01); *A61B 17/7037* (2013.01); *A61B 17/7079* (2013.01); *A61B 2019/307* (2013.01)

(58) Field of Classification Search
CPC ........... A61B 17/7032; A61B 17/7034; A61B 17/7035; A61B 17/7037; A61B 17/7038; A61B 17/8605; A61B 17/88
See application file for complete search history.

(56) References Cited

U.S. PATENT DOCUMENTS

| | | | |
|---|---|---|---|
| 5,207,678 A | 5/1993 | Harms et al. |
| 5,360,431 A | 11/1994 | Puno et al. |
| 5,474,555 A | 12/1995 | Puno et al. |
| 5,624,442 A | 4/1997 | Mellinger et al. |
| RE37,665 E | 4/2002 | Ralph et al. |
| 7,144,396 B2 | 12/2006 | Shluzas |
| 7,306,606 B2 | 12/2007 | Sasing |
| 7,338,491 B2 | 3/2008 | Baker et al. |

(Continued)

OTHER PUBLICATIONS

APEX Spine System Vertebral Body Derotation Surgical Technique, Jun. 2012.

*Primary Examiner* — Larry E Waggle, Jr.
(74) *Attorney, Agent, or Firm* — Alan W. Cannon; Law Office of Alan W. Cannon

(57) ABSTRACT

A surgical screw assembly is provided that includes a fastener including an elongate shaft having a proximal end and a distal end and a head at the proximal end. A tulip having an internal bearing surface and a distal end having a bore therethrough is provided to allow the distal end of the elongate shaft to pass therethrough. A first step feature located at a distal end portion of the bore and extending inwardly therefrom reduces the diameter of the bore to allow the distal end of the elongate shaft to pass therethrough, but prevents passage of the head therethrough. A second step feature located at a distal end portion of the bore, distally of the first step feature, further reduces the diameter of the bore to a dimension less than a dimension established by the first step feature, the further reduced dimension allowing the distal end of the elongate shaft to pass therethrough, but preventing passage of the head therethrough.

18 Claims, 15 Drawing Sheets

(56) References Cited

U.S. PATENT DOCUMENTS

| | | |
|---|---|---|
| 7,682,377 B2 | 3/2010 | Konieczynski et al. |
| 7,722,652 B2 | 5/2010 | Justis et al. |
| 7,727,261 B2 | 6/2010 | Barker et al. |
| 7,766,915 B2 | 8/2010 | Jackson |
| 7,785,354 B2 | 8/2010 | Biedermann et al. |
| 7,867,258 B2 | 1/2011 | Drewry et al. |
| 7,879,075 B2 | 2/2011 | Shluzas |
| 7,896,902 B2 | 3/2011 | Jeon et al. |
| 7,901,435 B2 | 3/2011 | Slivka et al. |
| 7,942,909 B2 | 5/2011 | Hammill, Sr. et al. |
| 7,951,173 B2 | 5/2011 | Hammill, Sr. et al. |
| 7,955,363 B2 | 6/2011 | Richelsoph |
| 7,967,849 B2 | 6/2011 | Carson et al. |
| 8,021,397 B2 | 9/2011 | Farris et al. |
| 8,057,519 B2 | 11/2011 | Justis et al. |
| 8,075,603 B2 | 12/2011 | Hammill, Sr. et al. |
| 8,080,036 B2 | 12/2011 | Shim et al. |
| 8,088,152 B2 | 1/2012 | Schumacher |
| 8,128,667 B2 | 3/2012 | Jackson |
| 8,137,387 B2 | 3/2012 | Garamszegi |
| 8,162,989 B2 | 4/2012 | Khalili |
| 8,167,910 B2 | 5/2012 | Nilsson |
| 2004/0102781 A1* | 5/2004 | Jeon ................................ 606/73 |
| 2007/0049933 A1 | 3/2007 | Ahn et al. |
| 2007/0073291 A1* | 3/2007 | Cordaro et al. ................. 606/61 |
| 2008/0234757 A1 | 9/2008 | Jacofsky et al. |
| 2009/0105769 A1 | 4/2009 | Rock et al. |
| 2009/0105771 A1 | 4/2009 | Lei et al. |
| 2010/0094343 A1 | 4/2010 | Pham et al. |
| 2010/0145394 A1 | 6/2010 | Harvey et al. |
| 2010/0204735 A1 | 8/2010 | Gephart et al. |
| 2010/0305621 A1 | 12/2010 | Wang et al. |
| 2011/0178558 A1 | 7/2011 | Barry |
| 2011/0196430 A1* | 8/2011 | Walsh et al. ................... 606/305 |
| 2013/0096624 A1* | 4/2013 | Di Lauro et al. .............. 606/279 |

\* cited by examiner

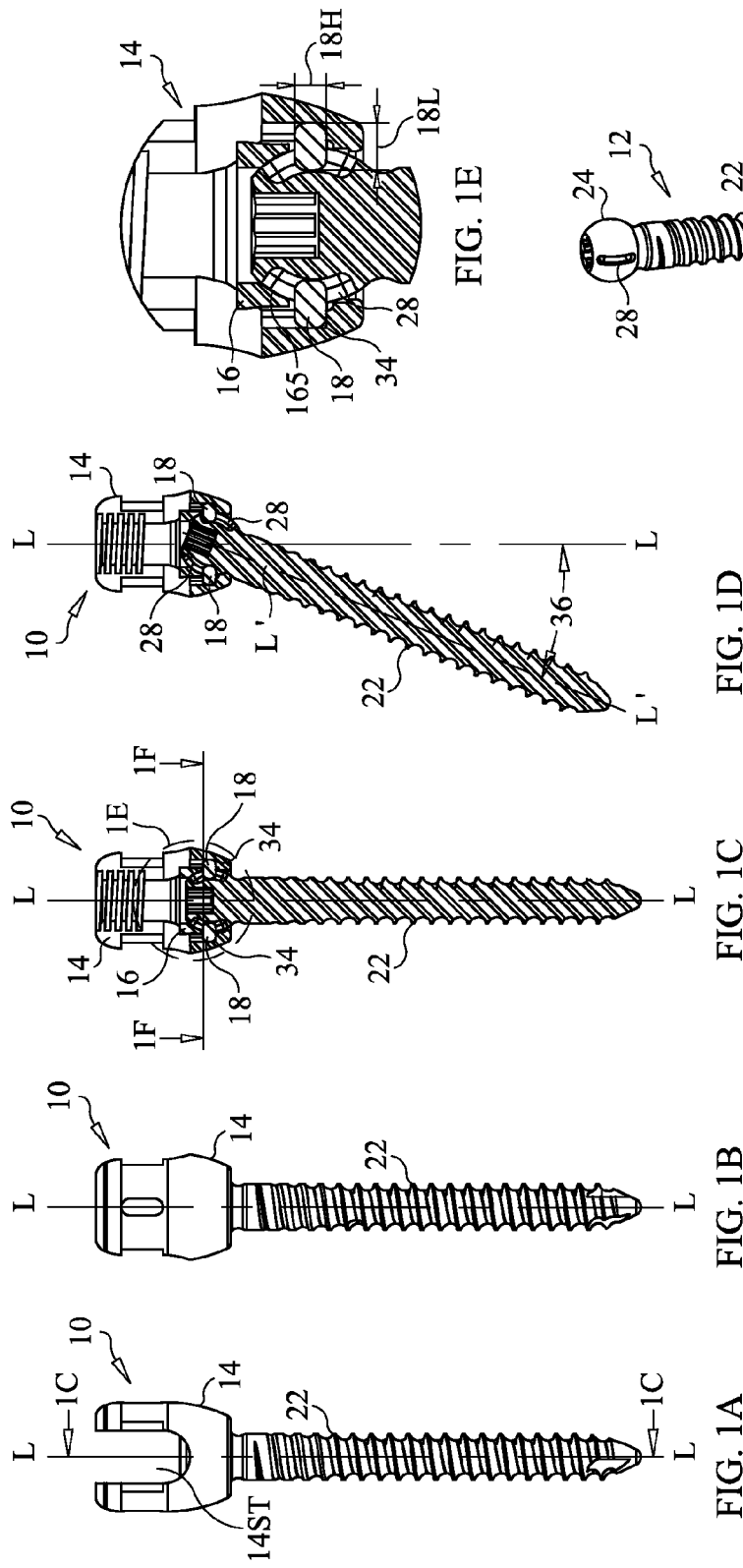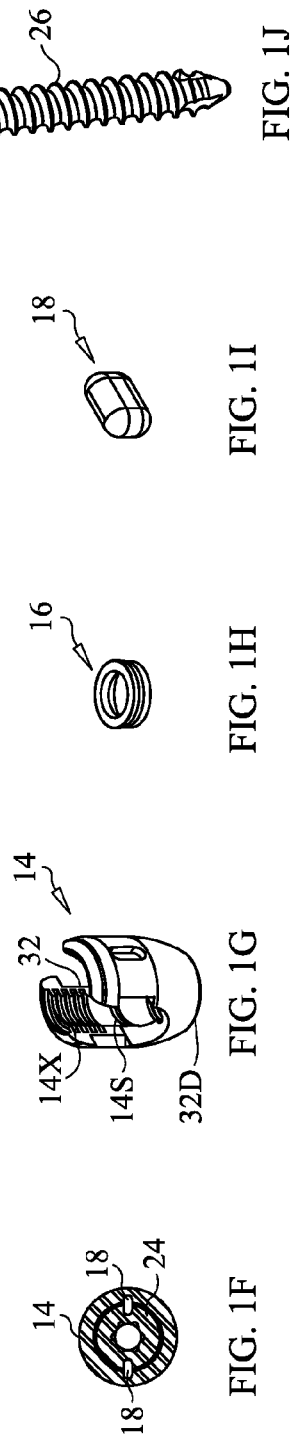

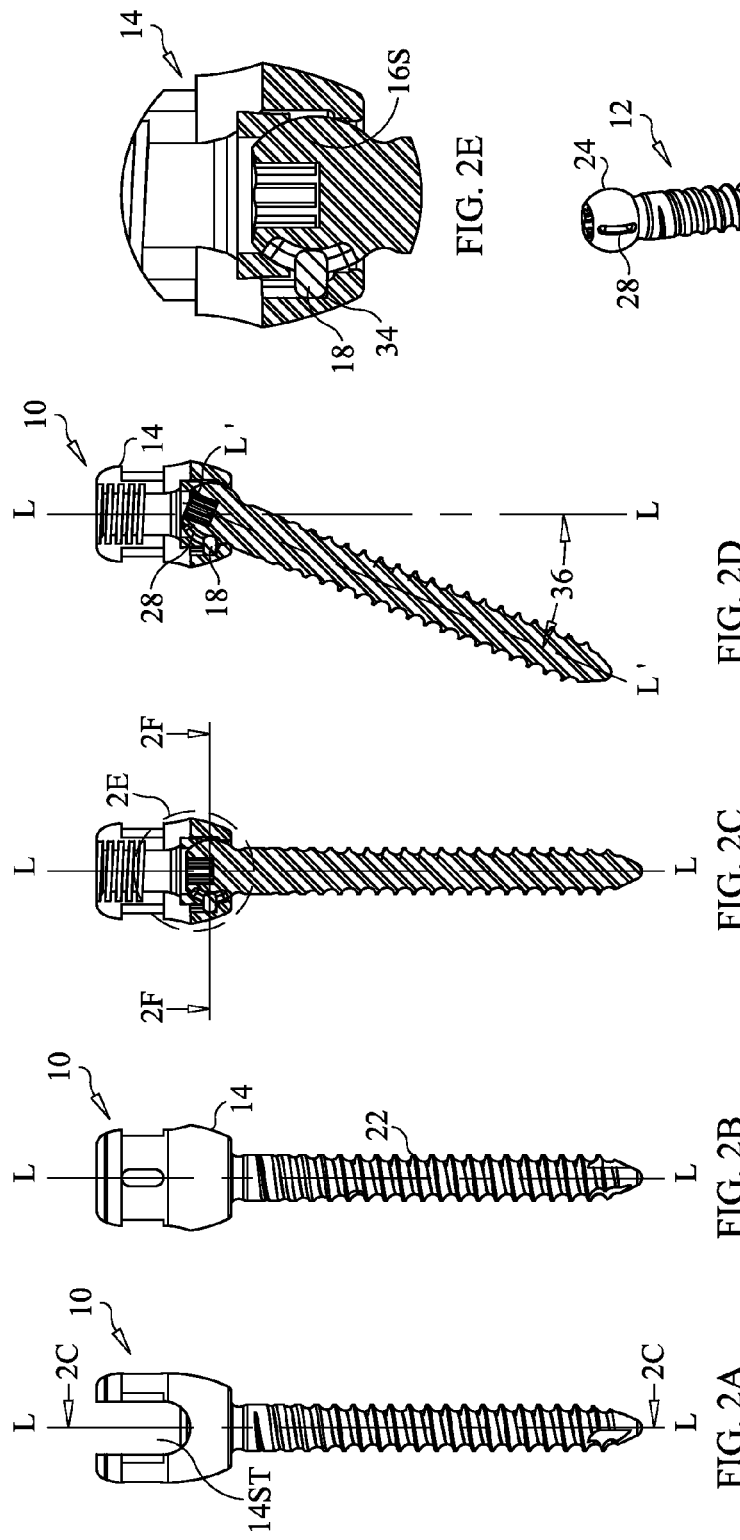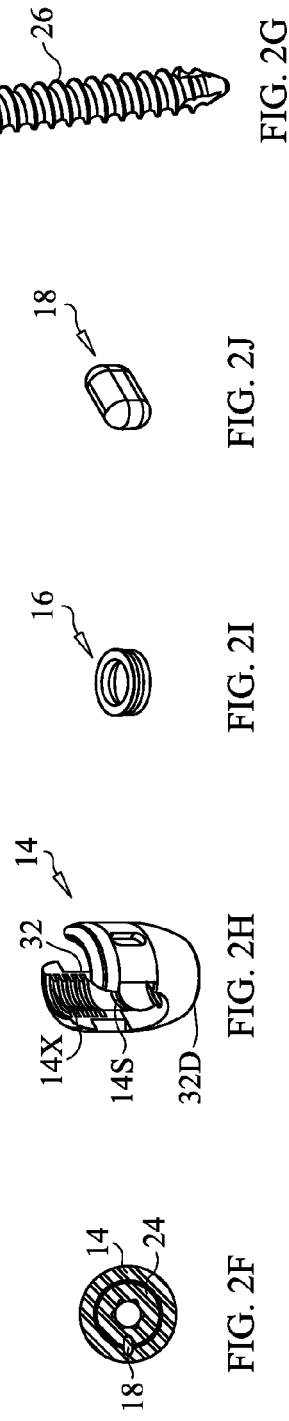

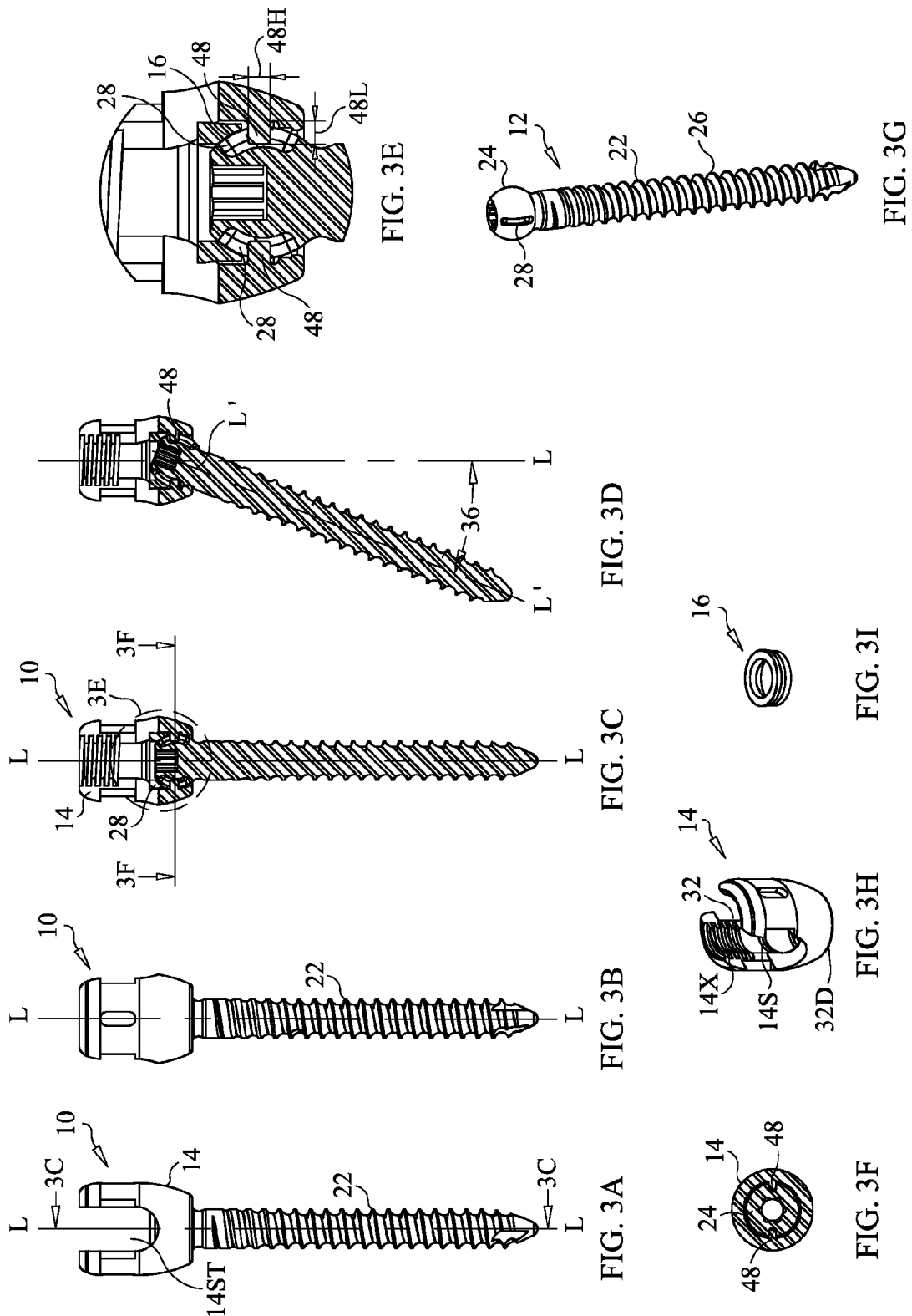

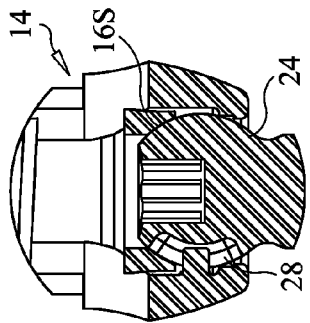
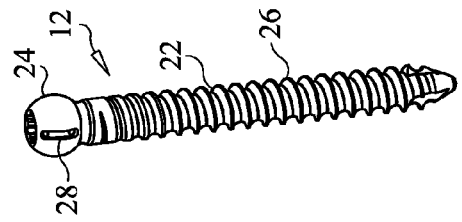
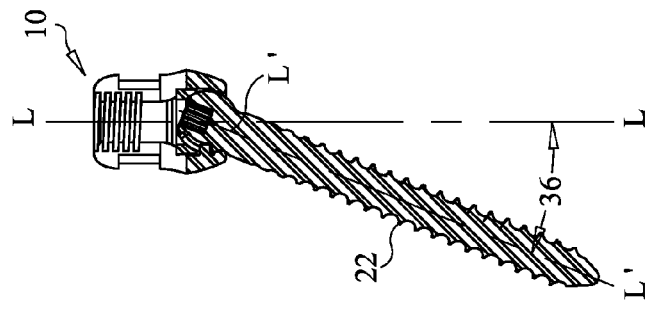
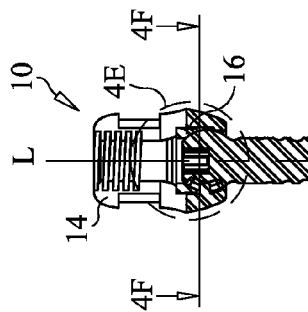
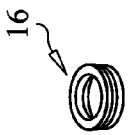
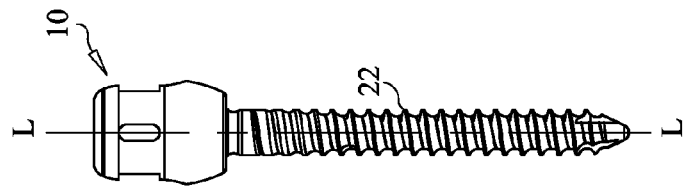
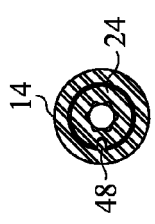
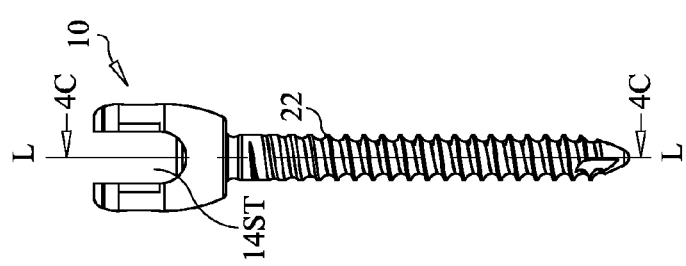

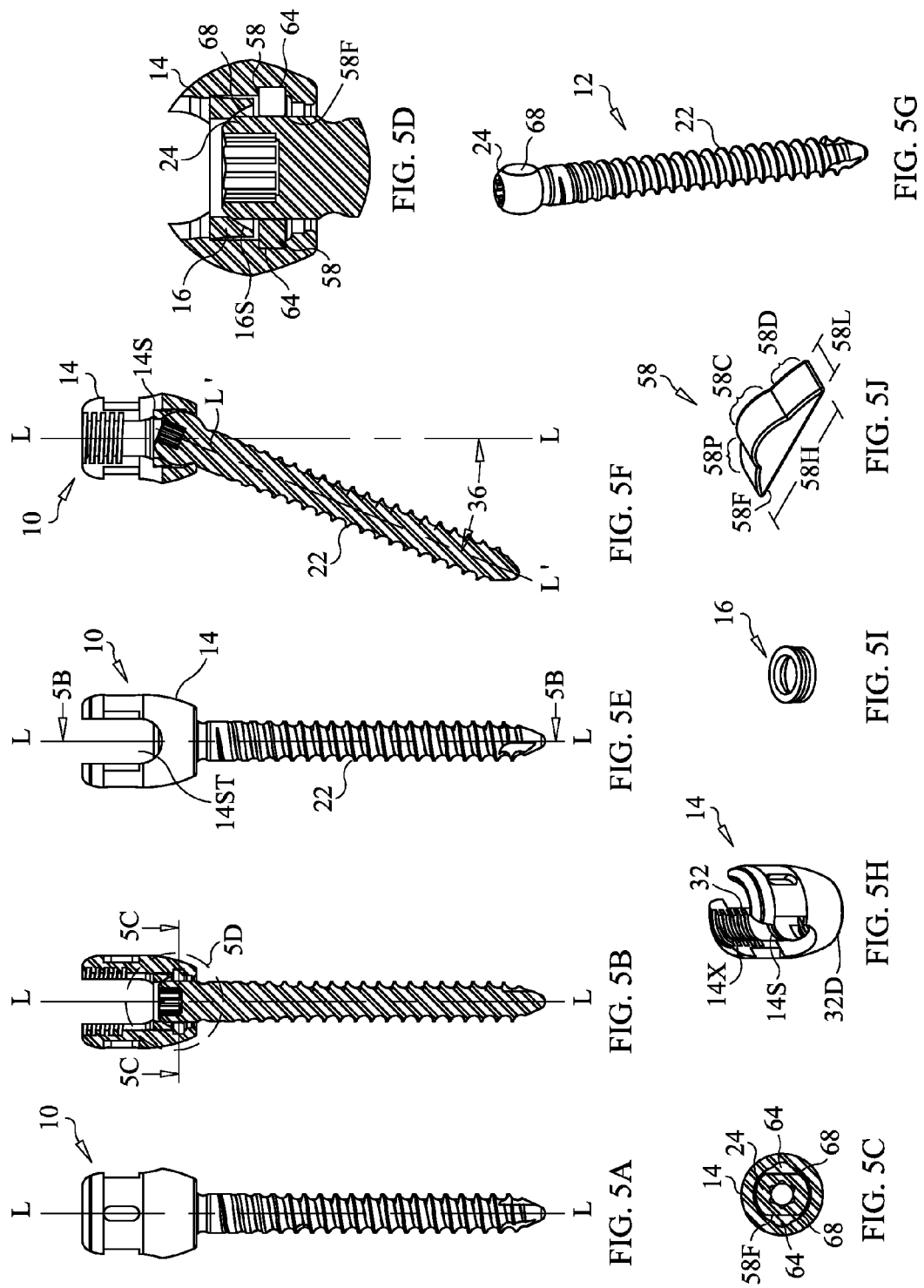

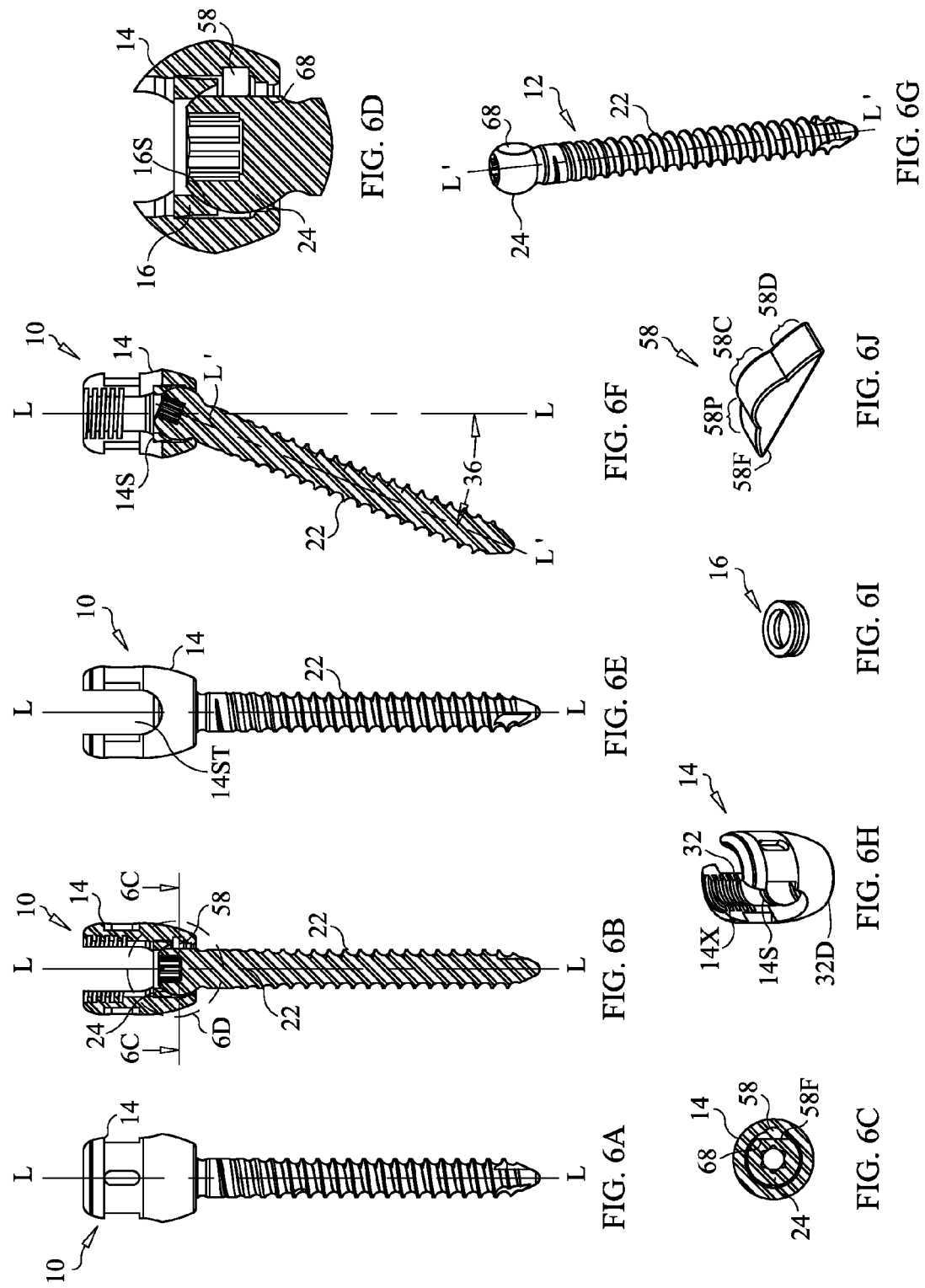

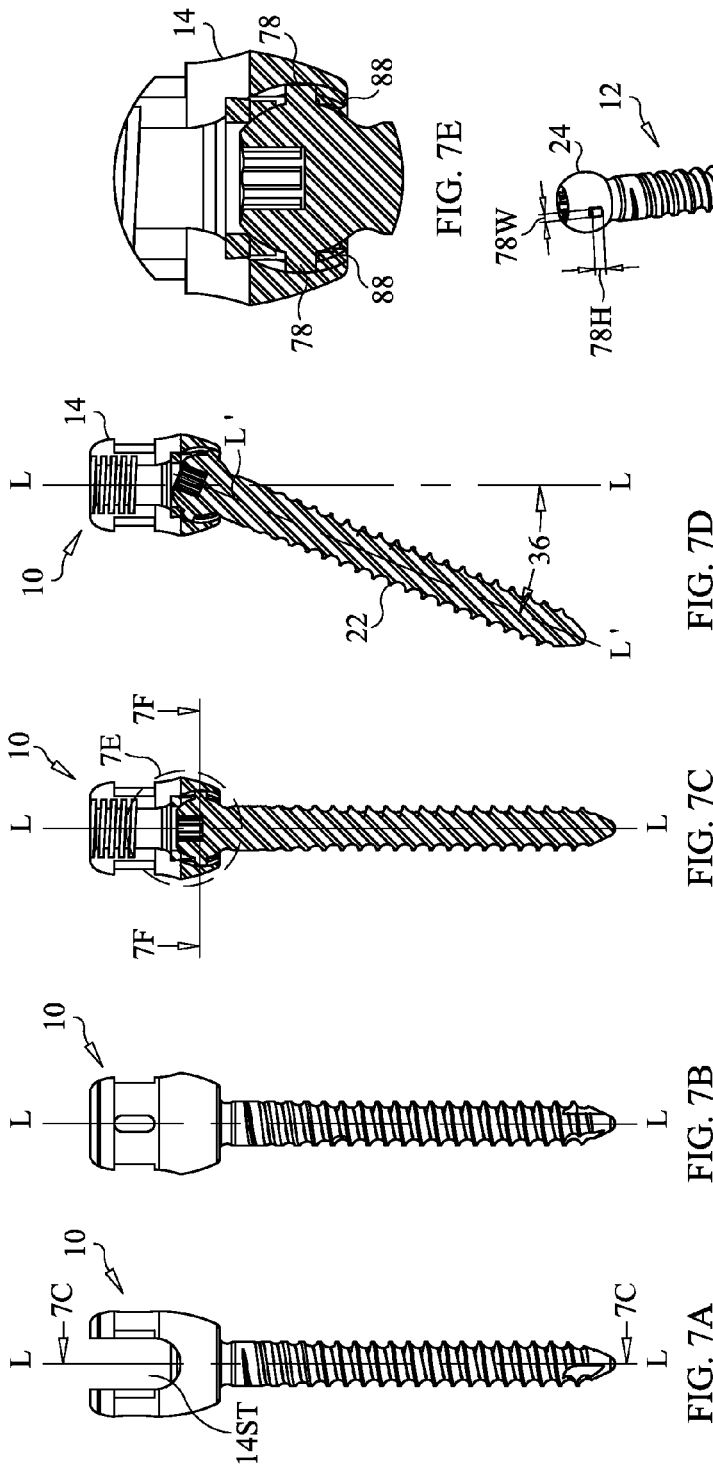

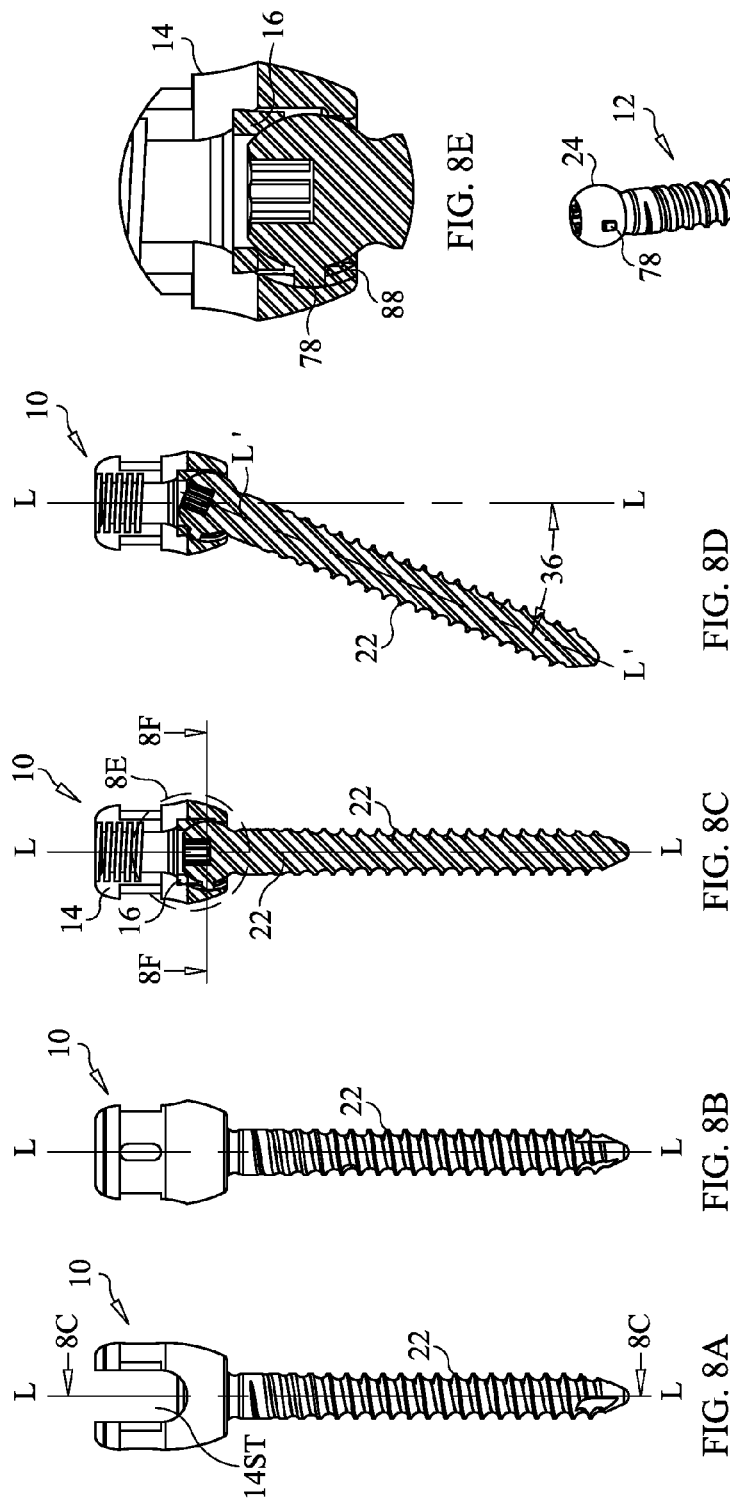

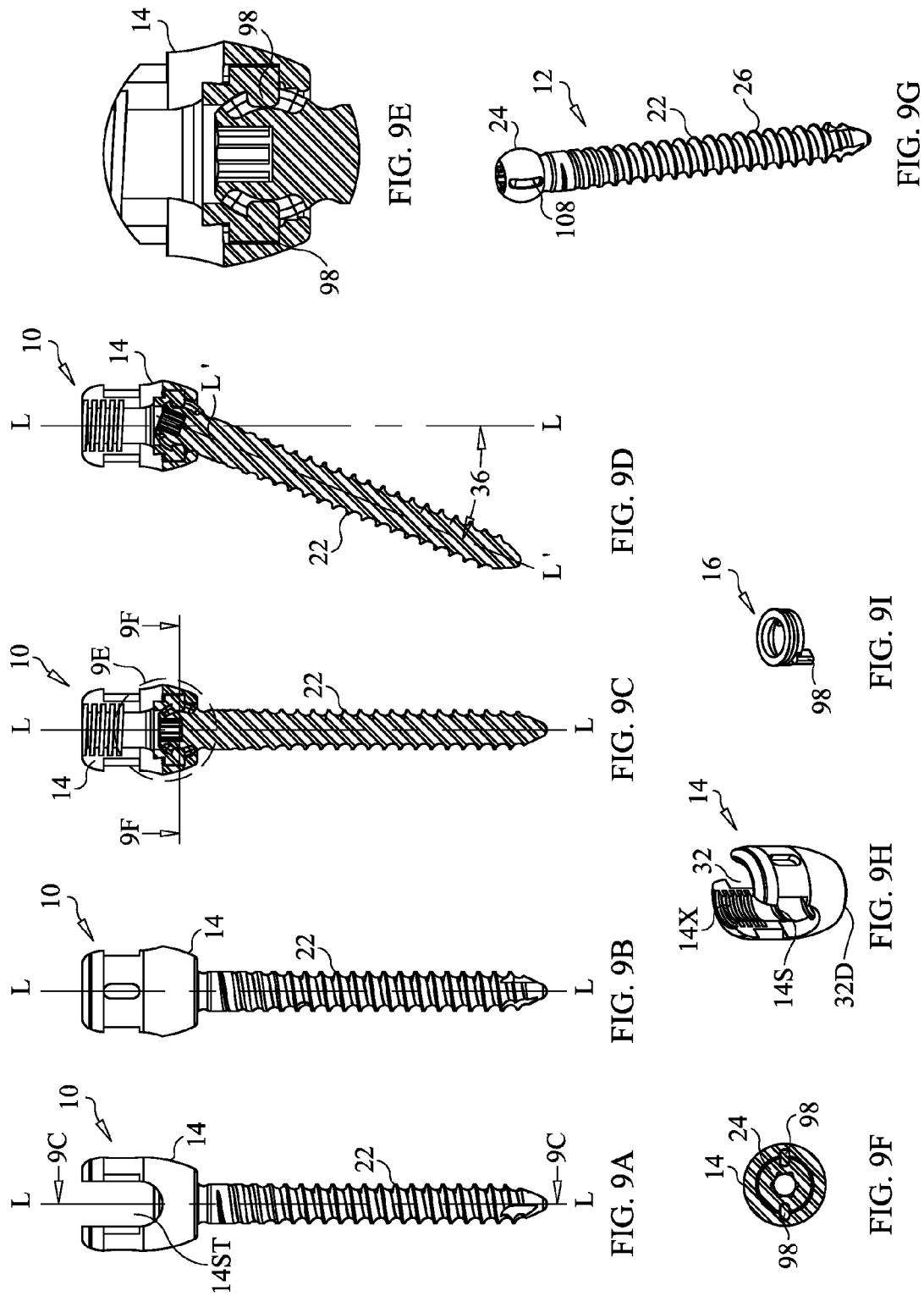

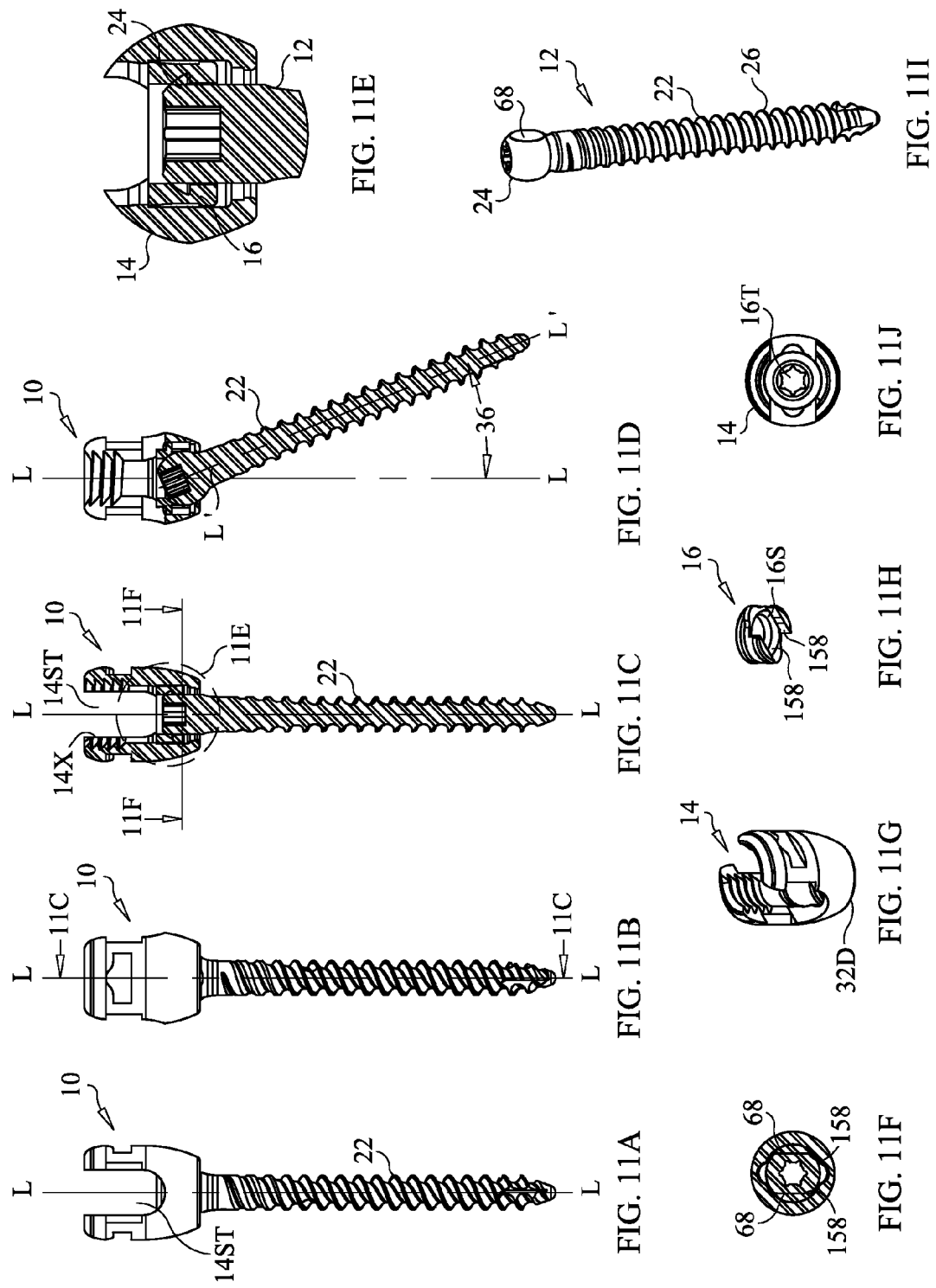

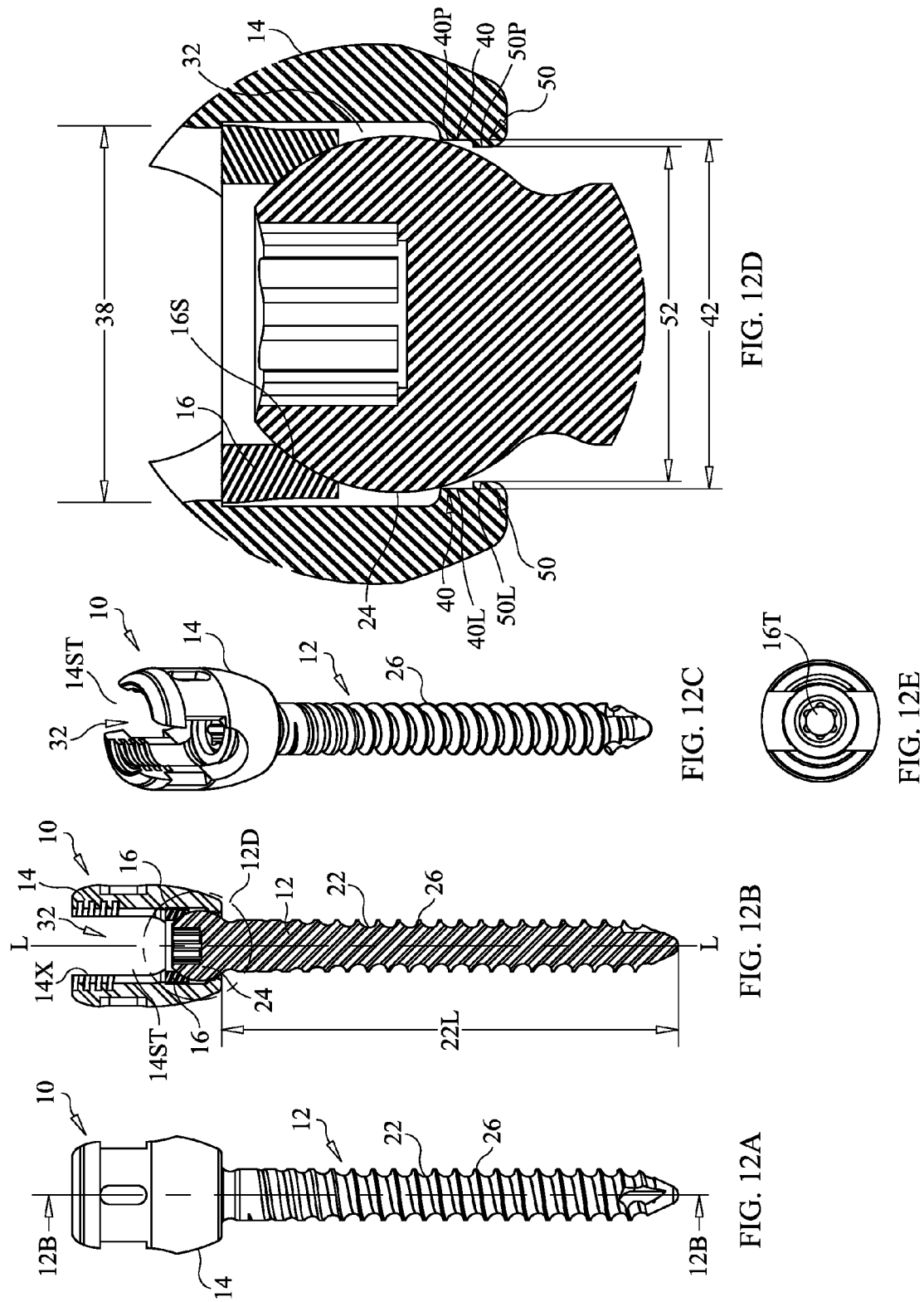

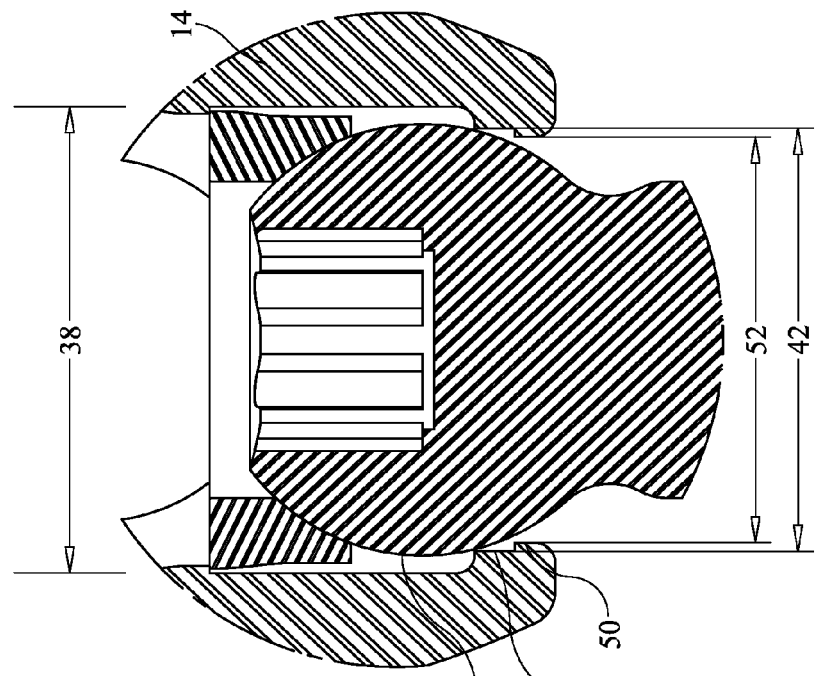
FIG. 13D
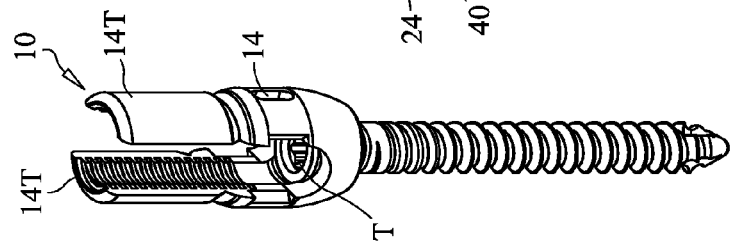
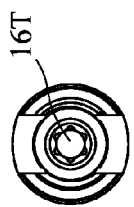
FIG. 13C
FIG. 13E
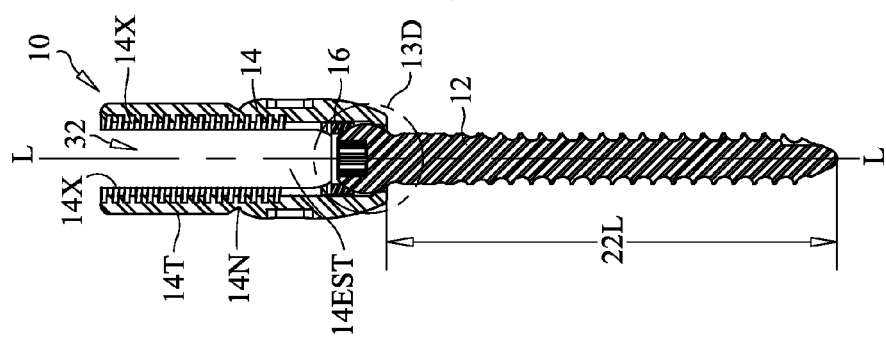
FIG. 13B
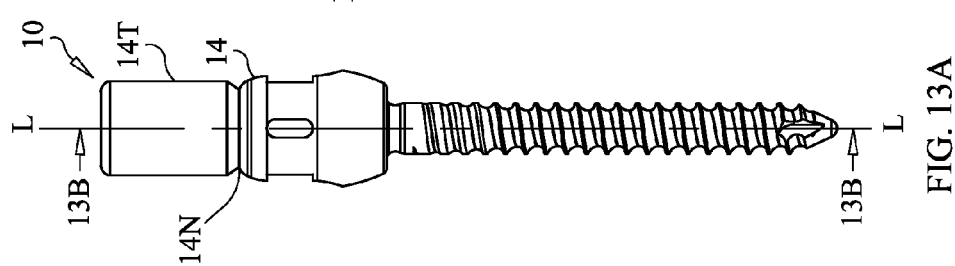
FIG. 13A

LOCKING FORCE AUGMENTATION FEATURES FOR SURGICAL SCREW ASSEMBLY

CROSS-REFERENCE

This application is a continuation-in-part application of co-pending application Ser. No. 13/570,374, filed Aug. 9, 2012 and titled "Uniplanar Surgical Screw Assembly", which is hereby incorporated herein, in its entirety, by reference thereto, and to which application we claim priority under 35 USC §120.

FIELD OF THE INVENTION

The present invention relates to the field of orthopedic surgery, in particular to devices, systems and assemblies for stabilizing and/or fixing bones and/or joints in a patient. More particularly, the present invention relates to polyaxial attachment assemblies including mechanisms for locking the same.

BACKGROUND OF THE INVENTION

The fixation and/or stabilization of bones and/or bone fragments is/are commonly required by orthopedic surgeons to treat injuries such as fractures or disease. To accomplish this, the bones/bone fragments can be joined by a rod, plate or the like, which is fixed to the bones/bone fragments via fasteners such as screws, pins or the like. The connection by the rod(s), plate(s) or the like maintains the bones/bone fragments in a desired orientation and/or at desired spacings, positions, etc. Different situations often require the adjustment of such spacings or orientations, or the removal of the apparatus, sometimes with replacement by another apparatus. For these reasons it is useful to provide fasteners that can be fixed or released, and can also articulate to adjust relative to the rod, plate, or the like, as required by the arrangement of the bones/bone fragments being treated.

In spinal surgery, it is often necessary to secure various implants to the vertebrae and interconnect the vertebrae by attaching one or more rods or plates to the implants. Due to the complex curvature of the spine, as well as irregularities of the same that often need to be treated, it is often difficult to align a rod or plate with all of the implants/fasteners fixed to the various vertebrae to be connected via the rod or plate. By providing fasteners that have some articulation ability, this allows more flexibility in joining the fasteners (and thus the vertebrae that they are attached to) to a rod or plate in the orientations needed.

In some surgeries, it is necessary to span multiple vertebrae of the spine with rods that provide stabilizing forces to the vertebrae to help maintain the desired orientations of the vertebrae o maintain a desired curvature in the spine. In these instances, uniplanar fasteners that allow pivoting in only one plane can be useful, as opposed to the more commonly used polyaxial screws, as polyaxial screws may be more likely to fail by rotating rather than withstanding a lateral force applied to the rod therethrough.

In any case, once the polyaxial or uniplanar fastener has been articulated to the desired angular position of the screw shaft relative to the tulip, there needs to be a mechanism for maintaining that angular position/orientation in a fixed manner, as the orientation should be maintained upon completing the procedure. There is a continuing need for improved fixation mechanisms to maintain fasteners in their desired orientation during use after completion of the procedure.

SUMMARY OF THE INVENTION

In one aspect of the present invention, a surgical screw assembly includes a fastener including an elongate shaft having a proximal end and a distal end and a head at the proximal end, the head having an external surface; a tulip having a tulip proximal end, a tulip distal end, an external surface and an internal bearing surface, the tulip distal end having a bore therethrough defining the internal bearing surface and having a diameter dimensioned to allow the distal end of the elongate shaft to pass therethrough; a first step feature located at a distal end portion of the bore and extending inwardly from the bore, the first step feature reducing the diameter of the bore to allow the distal end of the elongate shaft to pass therethrough, but prevent passage of the head therethrough as a portion of the first step feature contacts the external surface of the head; and a second step feature located at a distal end portion of the bore, distally of the first step feature, the second step feature further reducing the diameter of the bore to a dimension less than a dimension established by the first step feature, the further reduced dimension allowing the distal end of the elongate shaft to pass therethrough, but preventing passage of the head therethrough as a portion of the second step feature contacts the external surface of the head and a portion of the first step feature contacts the external surface of the head.

In at least one embodiment, in a unlocked configuration, the external surface of the head contacts the first step feature but does not contact the second step feature.

In at least one embodiment, in a locked configuration, the external surface of the head contacts the first step feature and the second step feature.

In at least one embodiment, the first step feature extends from at least two locations of the bore equally positioned relative to each other relative to a longitudinal axis of the bore, and the second step feature extends from at least two locations of the bore distal of the locations from which the first step feature extends and equally positioned relative to each other relative to the longitudinal axis of the bore.

In at least one embodiment, the at least two locations from which the first step feature extends are diametrically opposite one another, relative to a circumference of the bore and the at least two locations from which the second step feature extends are diametrically opposite one another, relative to the circumference of the bore.

In at least one embodiment, the first step feature extends continuously about the circumference of the bore and the second feature extends continuously about the circumference of the bore.

In at least one embodiment, in a locked configuration, a proximal end portion of the first step feature contacts the external surface of the head and a proximal end portion of the second step feature contacts the head.

In at least one embodiment, a longitudinal surface of the first step feature extends distally away from the proximal end portion of the first step feature contacting the external surface of the head and extends tangentially and distally away from the external surface of the head; and wherein a longitudinal surface of the second step feature extends distally away from the proximal end portion of the second step feature contacting the external surface of the head and extends tangentially and distally away from the external surface of the head.

In at least one embodiment, the first and second step feature portions engage the external surface of the head and lock the head, preventing movements of the head relative to the tulip when a compression force is applied to drive the external surface of the head and the first and second step features against one another under compression.

In at least one embodiment, upon removal of the compression force, the head is unlockable from the step features upon application of force to at least one of the tulip and the head.

In at least one embodiment, the tulip further comprises a slot extending therethrough normal to a longitudinal axis of the bore, the slot configured and dimensioned to receive a rod, plate, shaft or channel for connection to the assembly.

In at least one embodiment, the assembly further includes reduction tabs extending proximally of the tulip and extending the slot.

In at least one embodiment, the assembly further includes a saddle, the saddle being configured and dimensioned to be fitted in the tulip against the head of the fastener to prevent the head from moving proximally relative to the tulip.

In at least one embodiment, the saddle is configured to apply compression to the head to lock an orientation of the fastener relative to the tulip, by driving the external surface of the head against the first and second step features.

In at least one embodiment, the assembly includes a driving member configured to engage a proximal end portion of the tulip and to establish a driving force against a rod, shaft, plate or channel extending through a slot in the tulip.

In at least one embodiment, the driving force also drives the rod, shaft, plate or channel against the saddle and drives the saddle to apply the head against the first and second step features, thereby locking the head relative to the tulip.

In another aspect of the present invention, a method of locking a surgical screw assembly is provided, the method including: providing an assembly comprising: a fastener including an elongate shaft having a proximal end and a distal end and a head at the proximal end, the head having an external surface; a tulip having a tulip proximal end, a tulip distal end, an external surface and an internal bearing surface, the tulip distal end having a bore therethrough defining the internal bearing surface and having a diameter dimensioned to allow the distal end of the elongate shaft to pass therethrough; a first step feature located at a distal end portion of the bore and extending inwardly from the bore, the first step feature reducing the diameter of the bore to allow the distal end of the elongate shaft to pass therethrough, but prevent passage of the head therethrough as a portion of the first step feature contacts the external surface of the head; and a second step feature located at a distal end portion of the bore, distally of the first step feature, the second step feature further reducing the diameter of the bore to a dimension less than a dimension established by the first step feature, the further reduced diameter allowing the distal end of the elongate shaft to pass therethrough, but preventing passage of the head therethrough; wherein the assembly is provided in an unlocked configuration whereby the head can rotate relative to the tulip; and applying force to the head to drive the head and the step features under compression, thereby locking the assembly such that the head cannot rotate relative to the tulip.

In at least one embodiment, at least a portion of at least one of the external surface of the head and the first step feature deforms as a result of the applying force.

In at least one embodiment, at least a portion of at least one of the external surface of the head and the second step feature deforms as a result of the applying force.

In at least one embodiment, when in the unlocked configuration, the external surface of the head contacts the first step feature but does not contact the second step feature.

These and other features of the invention will become apparent to those persons skilled in the art upon reading the details of the assemblies and methods as more fully described below.

BRIEF DESCRIPTION OF THE DRAWINGS

FIG. 1A is a plan view of a uniplanar surgical screw assembly according to an embodiment of the present invention.

FIG. 1B shows the assembly of FIG. 1A having been rotated about its longitudinal axis L-L by ninety degrees, relative to the view shown in FIG. 1A.

FIG. 1C is a longitudinal sectional view of the embodiment of FIG. 1A taken along line 1C-1C.

FIG. 1D shows the assembly of FIG. 1C, after pivoting the shaft relative to the tulip.

FIG. 1E is an enlarged detailed view of the portion of FIG. 1C within circle 1E.

FIG. 1F is a cross sectional view of the assembly taken along line 1F-1F in FIG. 1C.

FIG. 1G is an isolated, perspective view of the tulip component of FIG. 1A.

FIG. 1H is an isolated, perspective view of the saddle component of FIG. 1A.

FIG. 1I is an isolated, perspective view of an insert component of FIG. 1A.

FIG. 1J is an isolated, perspective view of the fastener component of FIG. 1A.

FIG. 2A is a plan view of a uniplanar surgical screw assembly according to another embodiment of the present invention.

FIG. 2B shows the assembly of FIG. 2A having been rotated about its longitudinal axis L-L by ninety degrees, relative to the view shown in FIG. 2A.

FIG. 2C is a longitudinal sectional view of the embodiment of FIG. 2A taken along line 2C-2C.

FIG. 2D shows the assembly of FIG. 2C, after pivoting the shaft relative to the tulip.

FIG. 2E is an enlarged detailed view of the portion of FIG. 2C within circle 2E.

FIG. 2F is a cross sectional view of the assembly taken along line 2F-2F in FIG. 2C.

FIG. 2G is an isolated, perspective view of the fastener of FIG. 2A.

FIG. 2H is an isolated, perspective view of the tulip component of FIG. 2A.

FIG. 2I is an isolated, perspective view of the saddle component of FIG. 2A.

FIG. 2J is an isolated, perspective view of the insert component of FIG. 2A.

FIG. 3A is a plan view of a uniplanar surgical screw assembly according to another embodiment of the present invention.

FIG. 3B shows the assembly of FIG. 3A having been rotated about its longitudinal axis L-L by ninety degrees, relative to the view shown in FIG. 3A.

FIG. 3C is a longitudinal sectional view of the embodiment of FIG. 3A taken along line 3C-3C.

FIG. 3D shows the assembly of FIG. 3C, after pivoting the shaft relative to the tulip.

FIG. 3E is an enlarged detailed view of the portion of FIG. 3C within circle 3E.

FIG. 3F is a cross sectional view of the assembly taken along line 3F-3F in FIG. 3C.

FIG. 3G is an isolated, perspective view of the fastener of FIG. 3A.

FIG. 3H is an isolated, perspective view of the tulip component of FIG. 3A.

FIG. 3I is an isolated, perspective view of the saddle component of FIG. 3A.

FIG. 4A is a plan view of a uniplanar surgical screw assembly according to another embodiment of the present invention.

FIG. 4B shows the assembly of FIG. 4A having been rotated about its longitudinal axis L-L by ninety degrees, relative to the view shown in FIG. 4A.

FIG. 4C is a longitudinal sectional view of the embodiment of FIG. 4A taken along line 4C-4C.

FIG. 4D shows the assembly of FIG. 4C, after pivoting the shaft relative to the tulip.

FIG. 4E is an enlarged detailed view of the portion of FIG. 4C within circle 4E.

FIG. 4F is a cross sectional view of the assembly taken along line 4F-4F in FIG. 4C.

FIG. 4G is an isolated, perspective view of the fastener of FIG. 4A.

FIG. 4H is an isolated, perspective view of the tulip component of FIG. 4A.

FIG. 4I is an isolated, perspective view of the saddle component of FIG. 4A.

FIG. 5A is a plan view of a uniplanar surgical screw assembly according to another embodiment of the present invention.

FIG. 5B is a longitudinal sectional view of the embodiment of FIG. 5E taken along line 5B-5B.

FIG. 5C is a cross sectional view of the assembly taken along line 5C-5C in FIG. 5B.

FIG. 5D is an enlarged detailed view of the portion of FIG. 5B within circle 5D.

FIG. 5E shows the assembly of FIG. 5A having been rotated about its longitudinal axis L-L by ninety degrees, relative to the view shown in FIG. 5A.

FIG. 5F shows the assembly of FIG. 5B, after pivoting the shaft relative to the tulip.

FIG. 5G is an isolated, perspective view of the fastener of FIG. 5A.

FIG. 5H is an isolated, perspective view of the tulip component of FIG. 5A.

FIG. 5I is an isolated, perspective view of the saddle component of FIG. 5A.

FIG. 5J is an isolated, perspective view of a flat insert component of FIG. 5A.

FIG. 6A is a plan view of a uniplanar surgical screw assembly according to another embodiment of the present invention.

FIG. 6B is a longitudinal sectional view of the embodiment of FIG. 6E taken along line 6B-6B.

FIG. 6C is a cross sectional view of the assembly taken along line 6C-6C in FIG. 6B.

FIG. 6D is an enlarged detailed view of the portion of FIG. 6B within circle 6D.

FIG. 6E shows the assembly of FIG. 6A having been rotated about its longitudinal axis L-L by ninety degrees, relative to the view shown in FIG. 6A.

FIG. 6F shows the assembly of FIG. 6B, after pivoting the shaft relative to the tulip.

FIG. 6G is an isolated, perspective view of the fastener of FIG. 6A.

FIG. 6H is an isolated, perspective view of the tulip component of FIG. 6A.

FIG. 6I is an isolated, perspective view of the saddle component of FIG. 6A.

FIG. 6J is an isolated, perspective view of the flat insert component of FIG. 6A.

FIG. 7A is a plan view of a uniplanar surgical screw assembly according to another embodiment of the present invention.

FIG. 7B shows the assembly of FIG. 7A having been rotated about its longitudinal axis L-L by ninety degrees, relative to the view shown in FIG. 7A.

FIG. 7C is a longitudinal sectional view of the embodiment of FIG. 7A taken along line 7C-7C.

FIG. 7D shows the assembly of FIG. 7C, after pivoting the shaft relative to the tulip.

FIG. 7E is an enlarged detailed view of the portion of FIG. 7C within circle 7E.

FIG. 7F is a cross sectional view of the assembly taken along line 7F-7F in FIG. 7C.

FIG. 7G is an isolated, perspective view of the fastener of FIG. 7A.

FIG. 7H is an isolated, perspective view of the tulip component of FIG. 7A.

FIG. 7I is an isolated, perspective view of the saddle component of FIG. 7A.

FIG. 8A is a plan view of a uniplanar surgical screw assembly according to another embodiment of the present invention.

FIG. 8B shows the assembly of FIG. 8A having been rotated about its longitudinal axis L-L by ninety degrees, relative to the view shown in FIG. 8A.

FIG. 8C is a longitudinal sectional view of the embodiment of FIG. 8A taken along line 8C-8C.

FIG. 8D shows the assembly of FIG. 8C, after pivoting the shaft relative to the tulip.

FIG. 8E is an enlarged detailed view of the portion of FIG. 8C within circle 8E.

FIG. 8F is a cross sectional view of the assembly taken along line 8F-8F in FIG. 8C.

FIG. 8G is an isolated, perspective view of the fastener of FIG. 8A.

FIG. 8H is an isolated, perspective view of the tulip component of FIG. 8A.

FIG. 8I is an isolated, perspective view of the saddle component of FIG. 8A.

FIG. 9A is a plan view of a uniplanar surgical screw assembly according to another embodiment of the present invention.

FIG. 9B shows the assembly of FIG. 9A having been rotated about its longitudinal axis L-L by ninety degrees, relative to the view shown in FIG. 9A.

FIG. 9C is a longitudinal sectional view of the embodiment of FIG. 9A taken along line 9C-9C.

FIG. 9D shows the assembly of FIG. 9C, after pivoting the shaft relative to the tulip.

FIG. 9E is an enlarged detailed view of the portion of FIG. 9C within circle 9E.

FIG. 9F is a cross sectional view of the assembly taken along line 9F-9F in FIG. 9C.

FIG. 9G is an isolated, perspective view of the fastener of FIG. 9A.

FIG. 9H is an isolated, perspective view of the tulip component of FIG. 9A.

FIG. 9I is an isolated, perspective view of the saddle component of FIG. 9A.

FIG. 11A is a plan view of a uniplanar surgical screw assembly according to another embodiment of the present invention.

FIG. 11B is a view of the embodiment of FIG. 11A after rotation about the longitudinal axis by ninety degrees.

FIG. 11C is a longitudinal sectional view of the embodiment of FIG. 11B taken along line 11C-11C.

FIG. 11D is a view showing the fastener angled relative to the tulip, according to an embodiment of the present invention.

FIG. 11E is an enlarged detailed view of the portion of FIG. 11C within circle 11E.

FIG. 11F is a cross-sectional view of the assembly taken along line 11F-11F in FIG. 11C FIG. 11G is an isolated, perspective view of the tulip component of FIGS. 11A-11F.

FIG. 11H is an isolated, perspective view of the saddle component of FIGS. 11A-11F.

FIG. 11I is an isolated, perspective view of the fastener component of FIGS. 11A-11F.

FIG. 11J is a proximal end view of FIG. 11B.

FIG. 12A is a plan view of a surgical screw assembly according to another embodiment of the present invention.

FIG. 12B is a longitudinal sectional view of the assembly of FIG. 12A taken along line 12B-12B.

FIG. 12C is a perspective view of the assembly shown in FIG. 12A.

FIG. 12D is an enlarged detailed view of the portion of FIG. 12B within circle 12D.

FIG. 12E is a proximal end view of the assembly of FIG. 12A.

FIGS. 13A-13E illustrate a fastener 10 with extended reduction tabs 14T according to an embodiment of the present invention.

DETAILED DESCRIPTION OF THE INVENTION

Figure 10:
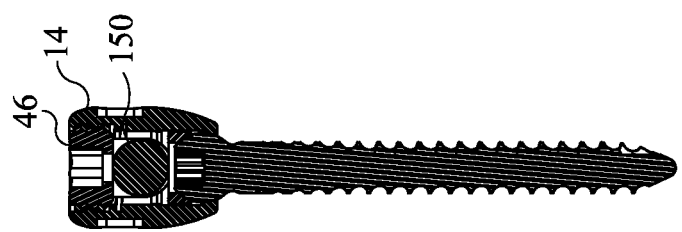
FIG. 10 is a longitudinal sectional view of an assembly locked to a rod according to an embodiment of the present invention.

Before the present assemblies, components and systems are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a location" includes a plurality of such locations and reference to "the screw" includes reference to one or more screws and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The embodiments described below are directed to uniplanar screw assemblies for use with an orthopedic rod. Although the following description is related to such use with an orthopedic rod, for example for surgical procedures treating the spine, it is noted that the present invention as described can be used in other applicable surgical procedures, such as in other orthopedic procedures for fixing and/or aligning bones, joints, etc. Furthermore, although the specific embodiments shown in the figures and described below employ a screw as a fastener, it should be understood that other types of fasteners or securing elements may alternatively or additionally be used, including, but not limited to lamina hooks, sacral blocks, etc.

Referring now to FIG. 1A, a plan view of a uniplanar surgical screw assembly 10 is shown, according to an embodiment of the present invention. FIG. 1B shows assembly 10 having been rotated about its longitudinal axis L-L by ninety degrees, relative to the view shown in FIG. 1A. The assembly 10 of the embodiment of FIGS. 1A-1J includes a fastener 12 (see the isolated view of FIG. 1J), a saddle-shaped tulip 14 (see the isolated view of FIG. 1G), a saddle 16 (see the isolated view of FIG. 1H) and a pair of inserts 18 (see isolated view of an insert 18 in FIG. 1I).

Fastener 12 includes an elongate shaft 22 having a proximal end and a distal end and a head 24 at the proximal end thereof. As shown, elongate shaft 22 is a screw shaft having threads 26 therealong. Head 24 includes a pair of slots 28 that extend in a proximal-distal direction aligned with the longitudinal axis L-L.

The tulip 14 has a bore 32 therethrough that is dimensioned to allow the distal end of elongate shaft 12 to pass therethrough, but the dimension of the distal opening 32D is smaller than the largest cross-sectional dimension of the head 24, and thereby prevents passage of the head 24 therethrough, as illustrated in FIGS. 1A-1E. Inserts 18 are fixed at 34 to tulip 14 as shown in FIG. 1C, so as to protrude into the bore 32. Slots 28 are configured and dimensioned to receive the protruding ends of inserts 18, to allow inserts 18 to freely slide therein in the proximal distal direction, but to prevent movements in any other directions. Inserts 18 may be fixed to tulip 14 by adhesives, welding, press fitting and/or other fixation expedients, preferably by press fitting into receptacles 34 formed in tulip 14. As shown in FIGS. 1C-1E, slots 28 are formed diametrically opposite one another, separated by 180 degrees around the head 24. This is necessary to allow both inserts 18 to slide in the same plane, resulting in an assembly that allows the elongate shaft 22 to pivot relative to the tulip 14 in one plane only. FIG. 1C shows a longitudinal sectional view of assembly 10 taken along line 1C-1C of FIG. 1A.

FIGS. 1A-1C illustrate the assembly 10 where the fastener 12 is aligned with the longitudinal axis L-L of the assembly 10 and tulip 14. FIG. 1D shows the longitudinal sectional view of FIG. 1C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14. The uniplanar range of motion may include angulation of up to about ±40°, typically a range of up to about ±22°, wherein the plus and minus values indicate the angle 36 in the direction shown in FIG. 1D and the same amount of angulation in the opposite direction in that plane.

Saddle 16 is configured and dimensioned to be fixed relative to tulip 14 while abutting the proximal portion of head 24 as shown in FIG. 1C. Saddle 16 has a concave distal surface 16s configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 1D. FIG. 1D illustrates a maximum angle 36 of pivoting, as inserts 18 make contact with the ends of slots 28, respectively. As shown in FIG. 1E, inserts 18 are centered in slots 28 when shaft 22 is aligned with the longitudinal axis L-L of the tulip 14. Alternatively, slots 28 could be asymmetrically formed so as to allow angulation 36 on one side of the longitudinal axis L-L to be greater than angulation on the other side (angulation the opposite direction).

In the embodiment shown, saddle 16 is a standard saddle and is configured and dimensioned to be retained by shoulder 14S when fitted into tulip 14, see FIG. 1G. The saddle-shaped tulip 14 further includes a slot 14ST passing therethrough, as shown in FIGS. 1A and 1G that is configured and dimensioned to receive an orthopedic rod or plate therein, in manners known in the art. Threading 14X allows a set screw 46 or the like to be torqued against the rod/plate, channel or shaft 150 to fix it relative to the tulip 14 (see FIG. 10). The saddle 16 is configured to apply compression to the head 24 to lock an orientation of the fastener 12 relative to the tulip 14, thereby even preventing the movement in the one plane that is otherwise allowed, and thus preventing movement in all planes. The set screw 46 presses on the rod, plate, channel or shaft 150 and the head 24 of the shaft is squeezed in between the saddle and the bottom of the tulip 14.

All components 12,14,16 and 18 of assembly 10 are preferably made of titanium. Alternatively, one or more components may be made of stainless steel, or other known, rigid materials used as substitute materials in the art, which may include other biocompatible metals, plastics and/or composites. The uniplanar angulation of assembly 10 may vary, but preferably has a range of about eighty degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 8.5 mm. The length of shaft 22 typically falls within a range of about 10 mm to about 100 mm. The height 18H of insert 18 is about 1 mm to about 2 mm, typically about 1.5 mm. The length 18L: of insert 18 is about 1.5 mm to about 3 mm, typically about 2.25 mm.

Referring now to FIG. 2A, a plan view of a uniplanar surgical screw assembly 10 is shown, according to another embodiment of the present invention. FIG. 2B shows assembly 10 having been rotated about its longitudinal axis L-L by ninety degrees, relative to the view shown in FIG. 2A. The assembly 10 of the embodiment of FIGS. 2A-2J includes a fastener 12 (see the isolated view of FIG. 2G), a saddle-shaped tulip 14 (see the isolated view of FIG. 2H), a saddle 16 (see the isolated view of FIG. 2I) and only one insert 18 (see isolated view in FIG. 2J), in contrast to the pair of inserts 18 employed in the embodiment of FIGS. 1A-1J.

Fastener 12 includes an elongate shaft 22 having a proximal end and a distal end and a head 24 at the proximal end thereof. As shown, elongate shaft 22 is a screw shaft having threads 26 therealong. Head 24 includes a slot 28 that extends in a proximal-distal direction aligned with the longitudinal axis L-L.

The tulip 14 has a bore 32 therethrough that is dimensioned to allow the distal end of elongate shaft 12 to pass therethrough, but the dimension of the distal opening 32D is smaller than the largest cross-sectional dimension of the head 24, and thereby prevents passage of the head 24 therethrough, as illustrated in FIGS. 2A-2E. Insert 18 is fixed at 34 to tulip 14 as shown in FIG. 2E, so as to protrude into the bore 32. Slot 28 is configured and dimensioned to receive the protruding end of insert 18, to allow insert 18 to freely slide therein in the proximal distal direction, but to prevent movements in any other directions. Insert 18 may be fixed to tulip 14 by adhesives, welding, press fitting and/or other fixation expedients, preferably by press fitting into receptacle 34 formed in tulip 14. Slot 28 is formed to allow insert 18 to slide only in a proximal-distal direction that permits pivoting of the shaft 22 relative to the tulip 14 in one plane only. FIG. 2C shows a longitudinal sectional view of assembly 10 taken along line 2C-2C of FIG. 2A. FIGS. 2A-2C illustrate the assembly 10 where the fastener 12 is aligned with the longitudinal axis L-L of the assembly 10 and tulip 14. FIG. 2D shows the longitudinal sectional view of FIG. 2C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 2C. Saddle 16 has a concave distal surface 16S configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 2D. FIG. 2D illustrates a maximum angle 36 of pivoting in one direction, as insert 18 makes contact with the end of slot 28. As shown in FIG. 2E, insert 18 is centered in slot 28 when shaft 22 is aligned with the longitudinal axis L-L of the tulip 14. Alternatively, slot 28 could be asymmetrically formed so as to allow angulation 36 on one side of the longitudinal axis L-L to be greater than angulation on the other side (angulation the opposite direction).

In the embodiment shown, saddle 16 is a standard saddle and is configured and dimensioned to be retained by shoulder 14S when fitted into tulip 14, see FIG. 2H. The saddle-shaped tulip 14 further includes a slot 14ST passing therethrough, as shown in FIGS. 2A and 2G that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes, by locking down with the set screw in a manner described above.

All components 12,14,16 and 18 of assembly 10 are preferably made of titanium. Alternatively, one or more components may be made of alternative materials, the same as described above with regard to the previous embodiment. The uniplanar angulation of assembly 10 may vary, but preferably has a range of about eighty (80) degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The height 18H of insert 18 is about 1 mm to about 2 mm, typically about 1.5 mm. The length 18L of insert 18 is about 1.5 mm to about 3 mm, typically about 2.25 mm.

FIG. 3A is a plan view of a uniplanar surgical screw assembly 10 according to another embodiment of the present invention. FIG. 3B shows assembly 10 having been rotated about its longitudinal axis L-L by ninety degrees, relative to the view shown in FIG. 3A. The assembly 10 of the embodiment of FIGS. 3A-3I includes a fastener 12 (see the isolated view of FIG. 3G), a saddle-shaped tulip 14 (see the isolated view of FIG. 3H), and a saddle 16 (see the isolated view of FIG. 3I). Rather than employing one or more inserts 18, the embodiment of FIGS. 3A-3I provides protrusions 48 integrally formed with tulip 14 and protruding into the open space formed by the bore 32, as shown in FIGS. 3C-3F.

Fastener 12 includes an elongate shaft 22 having a proximal end and a distal end and a head 24 at the proximal end thereof. As shown, elongate shaft 22 is a screw shaft having threads 26 therealong. Head 24 includes a pair of slots 28 that extend in a proximal-distal direction aligned with the longitudinal axis L-L.

The tulip 14 has a bore 32 therethrough that is dimensioned to allow the distal end of elongate shaft 22 to pass therethrough, but the dimension of the distal opening 32D is smaller than the largest cross-sectional dimension of the head 24, and thereby prevents passage of the head 24 therethrough, as illustrated in FIGS. 3A-3E. Slots 28 are configured and dimensioned to receive the protruding ends of protrusions 48, to allow protrusions 48 to freely slide therein in the proximal distal direction, but to prevent movements in any other directions. As shown in FIGS. 3C-3F, slots 28 are formed diametrically opposite one another, separated by 180 degrees around the head 24. This is necessary to allow both protrusions 48 to slide in the same plane, resulting in an assembly that allows the elongate shaft 22 to pivot relative to the tulip 14 in one plane only. FIG. 3C shows a longitudinal sectional view of assembly 10 taken along line 3C-3C of FIG. 1A. FIGS. 3A-3C illustrate the assembly 10 where the fastener 12 is aligned with the longitudinal axis L-L of the assembly 10 and tulip 14. FIG. 3D shows the longitudinal sectional view of FIG. 3C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 3C. Saddle 16 has a concave distal surface 16S configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 3D. FIG. 3D illustrates a maximum angle 36 of pivoting, as protrusions 48 make contact with the ends of slots 28, respectively. As shown in FIG. 3E (enlarged view of the portion of FIG. 3C identified within circle 3E), protrusions 48 are centered in slots 28 when shaft 22 is aligned with the longitudinal axis L-L of the tulip 14. Alternatively, slots 28 could be asymmetrically formed so as to allow angulation 36 on one side of the longitudinal axis L-L to be greater than angulation on the other side (angulation in the opposite direction).

In the embodiment shown, saddle 16 is a standard saddle and is configured and dimensioned to be retained by shoulder 14S when fitted into tulip 14, see FIG. 3H. The saddle-shaped tulip 14 further includes a slot 14ST passing therethrough, as shown in FIGS. 3A and 3H that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes, such as in a manner already previously described.

All components 12, 14, 16 and 48 of assembly 10 are preferably made of titanium. Alternatively, one or more components may be made of one or more alternative materials such as described in regard to previous embodiments. The uniplanar angulation of assembly 10 may vary, but preferably has a range of about eighty (80) degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The height 48H of protrusion 48 is about 1 mm to about 2 mm, typically about 1.5 mm. The length 48L: of protrusion 48 is about 1.5 mm to about 3 mm, typically about 2.25 mm.

FIG. 4A is a plan view of a uniplanar surgical screw assembly 10 according to another embodiment of the present invention. FIG. 4B shows assembly 10 having been rotated about its longitudinal axis L-L by ninety degrees, relative to the view shown in FIG. 4A. The assembly 10 of the embodiment of FIGS. 4A-4I includes a fastener 12 (see the isolated view of FIG. 4G), a saddle-shaped tulip 14 (see the isolated view of FIG. 4H), a saddle 16 (see the isolated view of FIG. 4I) and only one protrusion 48 (see FIGS. 4C-4F), in contrast to the pair of protrusions 48 employed in the embodiment of FIGS. 3A-3I.

Fastener 12 includes an elongate shaft 22 having a proximal end and a distal end and a head 24 at the proximal end thereof. As shown, elongate shaft 22 is a screw shaft having threads 26 therealong. Head 24 includes a slot 28 that extends in a proximal-distal direction aligned with the longitudinal axis L-L.

The tulip 14 has a bore 32 therethrough that is dimensioned to allow the distal end of elongate shaft 12 to pass therethrough, but the cross-sectional dimension of the distal opening 32D is smaller than the largest cross-sectional dimension of the head 24, and thereby prevents passage of the head 24 therethrough, as illustrated in FIGS. 4A-4E. Protrusion 48 is integral with tulip 14 and protrudes into the bore 32, as illustrated in FIGS. 4C-4F. Slot 28 is configured and dimensioned to receive the protruding end of protrusion 48, to allow protrusion 48 to freely slide therein in the proximal distal direction, but to prevent movements in any other directions. Slot 28 is formed to allow protrusion 48 to slide only in a proximal-distal direction that permits pivoting of the shaft 22 relative to the tulip 14 in one plane only. FIG. 4C shows a longitudinal sectional view of assembly 10 taken along line 4C-4C of FIG. 4A. FIGS. 4A-4C illustrate the assembly 10 where the fastener 12 is aligned with the longitudinal axis L-L of the assembly 10 and tulip 14. FIG. 4D shows the longitudinal sectional view of FIG. 4C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 4C. Saddle 16 has a concave distal surface 16S configured and dimensioned as a bearing surface to allow the convex curvature of head 24 to slide relative thereto. Accordingly, as shaft 22 is pivots relative to tulip 14, head 24 rotates against bearing surfaces of the tulip 14 and saddle 16, as illustrated in FIG. 4D. FIG. 4D illustrates a maximum angle 36 of pivoting in one direction, as protrusion 48 makes contact with the end of slot 28. As shown in FIG. 4E, protrusion 48 is centered in slot 28 when shaft 22 is aligned with the longitudinal axis L-L of the tulip 14. Alternatively, slot 28 could be asymmetrically formed so as to allow angulation 36 on one side of the longitudinal axis L-L to be greater than angulation on the other side (angulation in the opposite direction).

In the embodiment shown, saddle 16 is a standard saddle and is configured and dimensioned to be retained by shoulder 14S when fitted into tulip 14, see FIG. 4H. The saddle-shaped tulip 14 further includes a slot 14ST passing therethrough, as shown in FIGS. 2A and 2G that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes, such as in a manner described in previous embodiments.

All components 12,14,16 and 18 of assembly 10 are preferably made of titanium. One or more components may be made of an alternative material, like described in previous embodiments. The uniplanar angulation of assembly 10 may vary, but preferably has a range of about eighty (80) degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The height 18H of insert 18 is about 1 mm to about 2 mm, typically about 1.5 mm. The length 18L of insert 18 is about 1.5 mm to about 3 mm, typically about 2.25 mm.

FIG. 5A is a plan view of a uniplanar surgical screw assembly 10, according to another embodiment of the present invention. FIG. 5E shows assembly 10 having been rotated about its longitudinal axis L-L by ninety degrees, relative to the view shown in FIG. 5A. The assembly 10 of the embodiment of FIGS. 5A-5J includes a fastener 12 (see the isolated view of FIG. 5G), a saddle-shaped tulip 14 (see the isolated view of FIG. 5H), a saddle 16 (see the isolated view of FIG. 5I) and a pair of flat inserts 58 (see isolated view of a flat insert 58 in FIG. 5J).

Fastener 12 includes an elongate shaft 22 having a proximal end and a distal end and a head 24 at the proximal end thereof. As shown, elongate shaft 22 is a screw shaft having threads 26 therealong. Head 24 includes a pair of flats 68 on an otherwise convex surface, typically an otherwise spherical surface. The surfaces of flats 68 are substantially parallel to one another as shown in FIGS. 5C-5D.

The tulip 14 has a bore 32 therethrough that is dimensioned to allow the distal end of elongate shaft 12 to pass therethrough, but the cross-sectional dimension of the distal opening 32D is smaller than the largest cross-sectional dimension of the head 24, and thereby prevents passage of the head 24 therethrough, as illustrated in FIGS. 5A-5B and 5D-5F. Flat inserts 58 are received in receptacles 64 formed in tulip 14 as shown in FIGS. 5C-5D, in an orientation, so that the flat surface 58F of flat insert 58 interfaces with flat 68 of head 24, as also shown in FIGS. 5C-5D. The interaction between the flats 68 and flat sides 58F prevents all pivoting of the shaft 22 relative to the tulip 14, except for in one plane, that plane being parallel to the flats 68 and flat sides 58F. The non-flat side of insert 58 is received in receptacle 64 which has a shape that mates with the non-flat side of the insert 58.

The non-flat side of insert 58 is shaped and configured to prevent the flat insert 58 from sliding relative to the receptacle 64. In the embodiment shown in FIG. 5J, the non-flat side comprises a proximal end portion 58P, a central portion 58C, and a distal end portion 58D, wherein the central portion 58C extends further from the flat side 58D than the distances by which the proximal 58P and distal 58D end portions extend from the flat side 58F. In the embodiment shown in FIG. 5J, the central portion has a first curvature and the proximal and distal end portions have a second curvature, the first curvature having a smaller radius of curvature than the second curvature. In the embodiment of FIG. 5J, the non-flat side includes a bulbous portion 58C extending further from the flat side than an extent to which a remainder (58Pm 58D) of the non-flat side extends from the flat side 58F.

Flat inserts 58 may be fixed to tulip 14 by adhesives, welding, press fitting and/or other fixation expedients, or loosely fit within tulip 14. As shown in FIGS. 5C-5D, flats 68 are formed diametrically opposite one another on head 24, so as to be parallel to one another. This is necessary to allow the flats 68 to rotate relative to the flat inserts 58 as shaft 22 is pivoted relative to tulip 14, such as is shown in FIG. 5F. Thus, flats 68 and flat surface 58F are all oriented in substantially parallel planes to maintain uniplanar movement of the shaft 22 relative to the tulip 14.

FIG. 5B shows a longitudinal sectional view of assembly 10 taken along line 5B-5B of FIG. 5E. FIGS. 5A-5C illustrate the assembly 10 where the fastener 12 is aligned with the longitudinal axis L-L of the assembly 10 and tulip 14. FIG. 5F shows the longitudinal sectional view of FIG. 5B, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 5D. Saddle 16 has a concave distal surface 16s configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 5F. FIG. 5F illustrates a maximum angle 36 of pivoting. The limits of pivoting are established by the shaft 22 contacting against the tulip 14.

In the embodiment shown, saddle 16 is a standard saddle and is configured and dimensioned to be retained by shoulder 14S when fitted into tulip 14, see FIG. 5h. The saddle-shaped tulip 14 further includes a slot 14ST passing therethrough, as shown in FIGS. 5B and 5H that is configured and dimensioned to receive an orthopedic rod or plate therein, in manners known in the art. Threading 14X allows a set screw (not shown) or the like to be torqued against the rod/plate to fix it relative to the tulip 14.

All components 12,14,16 and 58 of assembly 10 are preferably made of titanium. One or more components may be made of an alternative material such as described above. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The length 58L of insert 58 is about 4.5 mm to about 6.5 mm, typically about 5.3 mm.

FIG. 6A is a plan view of a uniplanar surgical screw assembly 10, according to another embodiment of the present invention. FIG. 6E shows assembly 10 having been rotated about its longitudinal axis L-L by ninety degrees, relative to the view shown in FIG. 6A. The assembly 10 of the embodiment of FIGS. 6A-6J includes a fastener 12 (see the isolated view of FIG. 6G), a saddle-shaped tulip 14 (see the isolated view of FIG. 6H), a saddle 16 (see the isolated view of FIG. 6I) and a single flat insert 58 (see isolated view of FIG. 5J).

Fastener 12 includes an elongate shaft 22 having a proximal end and a distal end and a head 24 at the proximal end thereof. As shown, elongate shaft 22 is a screw shaft having threads 26 therealong. Head 24 includes a flat 68 on an otherwise convex surface, typically an otherwise spherical surface. The surface of flat 68 is substantially parallel to the longitudinal axis L'-L' of the fastener 12, as shown in FIG. 6G.

The tulip 14 has a bore 32 therethrough that is dimensioned to allow the distal end of elongate shaft 22 to pass therethrough, but the cross-sectional dimension of the distal opening 32D is smaller than the largest cross-sectional dimension of the head 24, and thereby prevents passage of the head 24 therethrough, as illustrated in FIGS. 6A-6B and 6D-6F. Flat insert 58 is received in receptacle 64 formed in tulip 14 as shown in FIGS. 6C-6D, in an orientation, so that the flat surface 58F of flat insert 58 interfaces with flat 68 of head 24, as also shown in FIGS. 6C-6D. The interaction between the flat 68 and flat side 58F prevents all pivoting of the shaft 22 relative to the tulip 14, except for in one plane, that plane being parallel to the flat 68 and flat side 58F. The non-flat side of insert 58 is received in receptacle 64 which has a shape that mates with the non-flat side of the insert 58.

The non-flat side of insert 58 is shaped and configured to prevent the flat insert 58 from sliding relative to the receptacle 64. In the embodiment shown in FIG. 6J, the non-flat side comprises a proximal end portion 58P, a central portion 58C, and a distal end portion 58D, wherein the central portion 58C extends further from the flat side 58D than the distances by which the proximal 58P and distal 58D end portions extend from the flat side 58F. In the embodiment shown in FIG. 6J, the central portion has a first curvature and the proximal and distal end portions have a second curvature, the first curvature having a smaller radius of curvature than the second curvature. In the embodiment of FIG. 5J, the non-flat side includes a bulbous portion 58C extending further from the flat side than an extent to which a remainder (58Pm 58D) of the non-flat side extends from the flat side 58F.

Flat insert 58 may be fixed to tulip 14 by adhesives, welding, press fitting and/or other fixation expedients, or may be loosely fitted in tulip 14. As shown in FIGS. 6C-6D, the surface of flat 68 is parallel to the flat surface 58F. This is necessary to allow the flat 68 to rotate relative to the flat insert 58 as shaft 22 is pivoted relative to tulip 14, such as is shown in FIG. 6F. Thus, flat 68 and flat surface 58F are oriented in substantially parallel planes to maintain uniplanar movement of the shaft 22 relative to the tulip 14.

FIG. 6B shows a longitudinal sectional view of assembly 10 taken along line 6B-6B of FIG. 6E. FIGS. 6A-6C illustrate the assembly 10 where the fastener 12 is aligned with the longitudinal axis L-L of the assembly 10 and tulip 14. FIG. 6F shows the longitudinal sectional view of FIG. 6B, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 6D. Saddle 16 has a concave distal surface 16s configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 6F. FIG. 6F illustrates a maximum angle 36 of pivoting, as limited by the shaft contacting the tulip.

In the embodiment shown, saddle 16 is a standard saddle and is configured and dimensioned to be retained by shoulder 14S when fitted into tulip 14, see FIGS. 6F and 6H. The saddle-shaped tulip 14 further includes a slot 14ST passing therethrough, as shown in FIGS. 6E and 6H that is configured and dimensioned to receive an orthopedic rod or plate therein, in manners known in the art. Threading 14X allows a set screw (not shown) or the like to be torqued against the rod/plate to fix it relative to the tulip 14.

All components 12,14,16 and 58 of assembly 10 are preferably made of titanium. One or more components may be made of an alternative material, such as described above with regard to previous embodiments. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The length 58L of insert 58 is about 4.5 mm to about 6.5 mm, typically about 5.3 mm.

FIG. 7A is a plan view of a uniplanar surgical screw assembly 10, according to another embodiment of the present invention. FIG. 7B shows assembly 10 having been rotated about its longitudinal axis L-L by ninety degrees, relative to the view shown in FIG. 7A. The assembly 10 of the embodiment of FIGS. 7A-7I includes a fastener 12 (see the isolated view of FIG. 7G), a saddle-shaped tulip 14 (see the isolated view of FIG. 7H), and a saddle 16 (see the isolated view of FIG. 7I).

Fastener 12 includes an elongate shaft 22 having a proximal end and a distal end and a head 24 at the proximal end thereof. As shown, elongate shaft 22 is a screw shaft having threads 26 therealong. Head 24 includes a pair of protrusions 78 extending from diametrically opposite sides of a convex surface. Protrusions 78 may be inserts fixed to head 24, but are preferably integrally formed therewith.

The tulip 14 has a bore 32 therethrough that is dimensioned to allow the distal end of elongate shaft 12 to pass therethrough, but the cross-sectional dimension of the distal opening 32D is smaller than the largest cross-sectional dimension of the head 24, and thereby prevents passage of the head 24 therethrough, as illustrated in FIGS. 7A-7E. Slots 88 are formed in the inner surface of tulip 14 as shown in FIG. 7E. Slots 88 each extend in a proximal-distal direction and are formed diametrically opposite one another. Slots 88 are configured and dimensioned to receive the protruding ends of protrusions 78, to allow protrusions 78 to freely slide therein in the proximal-distal directions, but to prevent movements in any other directions, i.e., only uniplanar pivoting is allowed. As noted, protrusions 78 are preferably integral with head 24, but when fixed thereto, may be fixed to head 24 by adhesives, welding, press fitting and/or other fixation expedients, preferably by press fitting into receptacles formed in the head 24. As shown in FIGS. 7C-7F, slots 88 are formed diametrically opposite one another, separated by 180 degrees around the tulip 14. This is necessary to allow both protrusions 78 to slide in the same plane, resulting in an assembly that allows the elongate shaft 22 to pivot relative to the tulip 14 in one plane only. FIG. 7C shows a longitudinal sectional view of assembly 10 taken along line 7C-7C of FIG. 7A. FIGS. 7A-7C illustrate the assembly 10 where the fastener 12 is aligned with the longitudinal axis L-L of the assembly 10 and tulip 14. FIG. 7D shows the longitudinal sectional view of FIG. 7C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 1C. Saddle 16 has a concave distal surface 16S configured and dimensioned as a bearing surface to allow the convex curvature of head 24 to slide relative thereto. Additionally, in this embodiment, saddle 16 includes a pair of diametrically opposed notches in the bottom surface thereof that are configured and dimensioned to slidably fit over the protrusions 78.

As shaft 22 is pivoted relative to tulip 14, head 24 rotates against bearing surfaces of the tulip 14 and saddle 16, as illustrated in FIG. 7D. FIG. 7D illustrates a maximum angle 36 of pivoting, as protrusions 78 make contact with the ends of slots 88, respectively. As shown in FIG. 7E, protrusions 78 are centered in slots 88 when shaft 22 is aligned with the longitudinal axis L-L of the tulip 14. Alternatively, slots 88 could be asymmetrically formed so as to allow angulation 36 on one side of the longitudinal axis L-L to be greater than angulation on the other side (angulation in the opposite direction).

In the embodiment shown, saddle 16 is configured and dimensioned to be retained by shoulder 14S when fitted into tulip 14, see FIGS. 7E and 7H. The saddle-shaped tulip 14 further includes a slot 14ST passing therethrough, as shown in FIGS. 7A and 7H that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes.

All components 12,14,16 and 78 of assembly 10 are preferably made of titanium. One or more components may be made of an alternative material, like previous embodiments described above. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The height 78H of protrusion 78 is in the range from about 1 mm to about 3 mm, typically about 2 mm. The width 78W of protrusion 78 is within a range of from about 1 mm to about 2.5 mm, typically about 1.75 mm.

FIG. 8A is a plan view of a uniplanar surgical screw assembly 10, according to another embodiment of the present invention. FIG. 8B shows assembly 10 having been rotated about its longitudinal axis L-L by ninety degrees, relative to the view shown in FIG. 8A. The assembly 10 of the embodiment of FIGS. 8A-8I includes a fastener 12 (see the isolated view of FIG. 8G), a saddle-shaped tulip 14 (see the isolated view of FIG. 8H), and a saddle 16 (see the isolated view of FIG. 8I).

Fastener 12 includes an elongate shaft 22 having a proximal end and a distal end and a head 24 at the proximal end thereof. As shown, elongate shaft 22 is a screw shaft having threads 26 therealong. Head 24 includes a single protrusion 78 extending from a side of a convex surface thereof. Protrusion 78 may be an insert fixed to head 24, but is preferably integrally formed therewith.

The tulip 14 has a bore 32 therethrough that is dimensioned to allow the distal end of elongate shaft 22 to pass therethrough, but the cross-sectional dimension of the distal opening 32D is smaller than the largest cross-sectional dimension of the head 24, and thereby prevents passage of the head 24 therethrough, as illustrated in FIGS. 8A-8E. A slot 88 is formed in the inner surface on one side of the tulip 14 as shown in FIG. 8E. Slot 88 extends in a proximal-distal direction and is formed in a direction parallel to the longitudinal axis L-L. Slot 88 is configured and dimensioned to receive the protruding end of protrusion 78, to allow protrusion 78 to freely slide therein in the proximal-distal directions, but to prevent movements in any other directions, i.e., only uniplanar pivoting is allowed. As noted, protrusion 78 is preferably integral with head 24, but when fixed thereto, may be fixed to head 24 by adhesives, welding, press fitting and/or other fixation expedients, preferably by press fitting into receptacles formed in the head 24. As shown in FIGS. 8C-8F, slot 88 is formed to receive protrusion 78 therein, to allow protrusion 78 to slide in a plane, resulting in an assembly that allows the elongate shaft 22 to pivot relative to the tulip 14 in one plane only. FIG. 8C shows a longitudinal sectional view of assembly 10 taken along line 8C-8C of FIG. 8A. FIGS. 8A-8C illustrate the assembly 10 where the fastener 12 is aligned with the longitudinal axis L-L of the assembly 10 and tulip 14. FIG. 8D shows the longitudinal sectional view of FIG. 8C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 8C. Saddle 16 has a concave distal surface 16S configured and dimensioned as a bearing surface to allow the convex curvature of head 24 to slide relative thereto. Additionally, in this embodiment, saddle 16 includes a notch 90 in the bottom surface thereof that is configured and dimensioned to slidably fit over the protrusion 78.

As shaft 22 is pivoted relative to tulip 14, head 24 rotates against bearing surfaces of the tulip 14 and saddle 16, as illustrated in FIG. 8D. FIG. 8D illustrates a maximum angle 36 of pivoting, as protrusion 78 makes contact with the end of slot 88. As shown in FIG. 8E, protrusion 78 is centered in slot 88 when shaft 22 is aligned with the longitudinal axis L-L of the tulip 14. Alternatively, slot 88 could be asymmetrically formed so as to allow angulation 36 on one side of the longitudinal axis L-L to be greater than angulation on the other side (angulation in the opposite direction).

In the embodiment shown, saddle 16 is configured and dimensioned to be retained by shoulder 14S when fitted into tulip 14, see FIGS. 8E and 8H. The saddle-shaped tulip 14 further includes a slot 14ST passing therethrough, as shown in FIGS. 8A and 8H that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes.

All components 12,14,16 and 78 of assembly 10 are preferably made of titanium. One or more components may be made of an alternative material such as described above with regard to previous embodiments. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The height 78H of protrusion 78 is in the range from about 1 mm to about 3 mm, typically about 2 mm. The width 78W of protrusion 78 is within a range of from about 1 mm to about 2.5 mm, typically about 1.75 mm.

FIG. 9A is a plan view of a uniplanar surgical screw assembly 10 according to another embodiment of the present invention. FIG. 9B shows assembly 10 having been rotated about its longitudinal axis L-L by ninety degrees, relative to the view shown in FIG. 9A. The assembly 10 of the embodiment of FIGS. 9A-9I includes a fastener 12 (see the isolated view of FIG. 9G), a saddle-shaped tulip 14 (see the isolated view of FIG. 9H), and a saddle 16 (see the isolated view of FIG. 9I). Rather than employing one or more inserts 18, the embodiment of FIGS. 9A-9I provides protrusions 98 integrally formed with saddle 16 and protruding inwardly, see FIGS. 9E, 9F and 9I.

Fastener 12 includes an elongate shaft 22 having a proximal end and a distal end and a head 24 at the proximal end thereof. As shown, elongate shaft 22 is a screw shaft having threads 26 therealong. Head 24 includes a pair of slots 108 that extend in a proximal-distal direction aligned with the longitudinal axis L-L.

The tulip 14 has a bore 32 therethrough that is dimensioned to allow the distal end of elongate shaft 22 to pass therethrough, but the cross-sectional dimension of the distal opening 32D is smaller than the largest cross-sectional dimension of the head 24, and thereby prevents passage of the head 24 therethrough, as illustrated in FIGS. 9A-9E. Slots 28 are configured and dimensioned to receive the protruding ends of protrusions 98, to allow protrusions 98 to freely slide therein in the proximal-distal direction, but to prevent movements in any other directions. As shown in FIGS. 9C-9F, slots 28 are formed diametrically opposite one another, separated by 180 degrees around the head 24. This is necessary to allow both protrusions 98 to slide in the same plane, resulting in an assembly that allows the elongate shaft 22 to pivot relative to the tulip 14 in one plane only. FIG. 9C shows a longitudinal sectional view of assembly 10 taken along line 9C-9C of FIG. 9A. FIGS. 9A-9C illustrate the assembly 10 where the fastener 12 is aligned with the longitudinal axis L-L of the assembly 10 and tulip 14. FIG. 9D shows the longitudinal sectional view of FIG. 9C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 9C. Saddle 16 has a concave distal surface 16S configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 9D. FIG. 9D illustrates a maximum angle 36 of pivoting, as protrusions 98 make contact with the ends of slots 208, respectively. As shown in FIG. 9E (enlarged view of the portion of FIG. 9C identified within circle 9E), protrusions 98 are centered in slots 208 when shaft 22 is aligned with the longitudinal axis L-L of the tulip 14. Alternatively, slots 108 could be asymmetrically formed so as to allow angulation 36 on one side of the longitudinal axis L-L to be greater than angulation on the other side (angulation in the opposite direction).

In the embodiment shown, saddle 16 is configured and dimensioned to be retained by shoulder 14S when fitted into tulip 14, see FIGS. 9E and 9H. The saddle-shaped tulip 14 further includes a slot 14ST passing therethrough, as shown in FIGS. 9A and 9H that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes.

All components 12,14 and 16 of assembly 10 are preferably made of titanium. Alternatively, one or more components may be made of an alternative material, like previous embodiments described. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The height 18H of insert 18 is about 1 mm to about 2 mm, typically about 1.5 mm. The length 18L: of insert 18 is about 1.5 mm to about 3 mm, typically about 2.25 mm.

FIG. 11A is a plan view of a uniplanar surgical screw assembly 10, according to another embodiment of the present invention. FIG. 11B shows assembly 10 having been rotated about its longitudinal axis L-L by ninety degrees, relative to the view shown in FIG. 11A. The assembly 10 of the embodiment of FIGS. 11A-11IJ includes a fastener 12 (see the isolated view of FIG. 11I), a saddle-shaped tulip 14 (see the isolated view of FIG. 11G), and a saddle 16 (see the isolated view of FIG. 11H).

Fastener 12 includes an elongate shaft 22 having a proximal end and a distal end and a head 24 at the proximal end thereof. As shown, elongate shaft 22 is a screw shaft having threads 26 therealong. Head 24 includes a pair of opposing flats 68 on an otherwise convex surface, typically an otherwise spherical surface. The surfaces of flats 68 are substantially parallel to one another as shown in FIG. 11F.

The tulip 14 has a bore 32 therethrough that is dimensioned to allow the distal end of elongate shaft 12 to pass therethrough, but the cross-sectional dimension of the distal opening 32D is smaller than the largest cross-sectional dimension of the head 24, and thereby prevents passage of the head 24 therethrough, as illustrated in FIGS. 11A-11E. Saddle 16 includes a pair of opposing flats 158 (see FIG. 11H) that interface with flats 68 (see FIG. 11F). Saddle 16 is rotationally fixed relative to tulip 14 when assembly 10 is assembled (see FIG. 11E). The interface between flats 158 and flats 68, combined with the prevention of saddle 16 from rotating relative to tulip 14, prevents all pivoting of the shaft 22 relative to the tulip 14, except for in one plane, that plane being parallel to the flats 68 and flats 158.

FIG. 11C shows a longitudinal sectional view of assembly 10 taken along line 11C-11C of FIG. 11B. FIGS. 11A-11C illustrate the assembly 10 where the fastener 12 is aligned with the longitudinal axis L-L of the assembly 10 and tulip 14. FIG. 11D shows the assembly 10 after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 11E. Saddle 16 has a concave distal surface 16*s* configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 11D. FIG. 11D illustrates a maximum angle 36 of pivoting. The limits of pivoting are established by the shaft 22 contacting against the tulip 14.

In the embodiment shown, the saddle-shaped tulip 14 includes a slot 14ST passing therethrough, as shown in FIGS. 11A and 11C that is configured and dimensioned to receive an orthopedic rod or plate therein, in manners known in the art (an example of which is shown in FIG. 10). Threading 14X allows a set screw 46 (see FIG. 10) or the like to be torqued against the rod/plate to fix it relative to the tulip 14.

All components 12, 14 and 16 of assembly 10 are preferably made of titanium. One or more components may be made of an alternative material such as described above. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The length of flat 158 is about 4.5 mm to about 6.5 mm, typically about 5.0 mm.

FIG. 11J is a proximal end view of the assembly of FIG. 11B illustrating a tool interface 16T that can be interfaced by a tool to drive the fastener 12 into the bone. The present invention is not limited to this type of interface as any other equivalent type of torqueing interface could be used.

FIG. 12A is a plan view of a surgical screw assembly 10, according to another embodiment of the present invention. In the embodiment of FIG. 12A, the surgical screw assembly is a polyaxial surgical screw assembly, meaning that, in an unlocked condition, shaft 22 can pivot relative to tulip 14 in any plane. However, the locking force augmentation features (e.g., the step features, arrangement and functioning of the tulip and head, and methods of providing enhanced locking force) as described with this embodiment are equally applicable to uniplanar surgical screw assemblies, such as those described above, and are generally applicable to all polyaxial and uniplanar screw assemblies to provide enhanced locking force. FIG. 12B is a longitudinal sectional view of the assembly 10 taken along line 12B-12B in FIG. 12A. FIG. 12C is a perspective view of the assembly 10 of FIG. 12A.

The assembly 10 of the embodiment of FIGS. 12A-12G includes a fastener 12 including an elongate shaft 22 and a head 24 at a proximal end of the shaft 22. As shown, elongate shaft 22 is a screw shaft having threads 26 therealong. Head 24 is substantially spherical, having a convex external surface. A tulip 14 has a bore 32 therethrough that defines a bearing surface against which head 24 can rotate when assembly 10 is in an unlocked configuration. Bore 32 is dimensioned to allow the distal end of elongate shaft 12 to pass therethrough as well as to allow the head 24 to be inserted into the tulip 14.

FIG. 12D is an enlarged detailed view of the portion of FIG. 12B within circle 12D. A first step feature 40 is located at a distal end portion of bore 32 and extends inwardly therefrom. The first step feature 40 reduces the diameter 38 of bore 32 to a dimension 42 that allows the distal end of the elongate shaft to pass therethrough, and allows all of the shaft 22 to pass therethrough, but prevents passage of head 24 therethrough as a portion of the first step feature contacts the external surface of the head, as shown in FIG. 12D. A second step feature 50 is located at a distal end portion of bore 32, distally of first step feature 40. Second step feature 50 further reduces the diameter of bore 32 to a dimension 52 less than dimension 42 established by first step feature, the further reduced dimension 52 allowing the distal end of the elongate shaft 22 to pass therethrough, and allows all of the shaft 22 to pass therethrough, but prevents passage of head 24 therethrough.

FIG. 12D illustrates the assembly in an unlocked configuration. In an unlocked configuration, as noted above, head 24 can be rotated relative to tulip 14 so as to pivot the shaft 22 relative to the longitudinal axis L-L of the tulip 14. As also noted above, in this embodiment, shaft 22 can be pivoted in any plane when assembly 10 is in an unlocked configuration. However, the step features described with regard to this embodiment can be likewise installed in a uniplanar assembly, wherein, in an unlocked configuration, shaft 22 would be allowed to pivot in a single plane only.

FIG. 12E is a top view of the assembly 10 of FIG. 12A. A tool interface 16T is provided in the proximal end of head 24 that can be interfaced by a tool to drive the fastener 12 into the bone. The present invention is not limited to this type of interface as any other equivalent type of torqueing interface could be used.

In the unlocked configuration shown in FIGS. 12B and 12D, the external surface of head 24 contacts the first step feature 40. In a preferred embodiment, the external surface of head 24 does not contact the second step feature 50, as shown in FIG. 12D. Alternatively, step feature 50 may be configured to extend further into the bore 32 so that the external surface of head 24 contacts both the first and second step features when in an unlocked configuration. However, in this alternative arrangement, final locking would be even more enhanced relative to the embodiment described in FIG. 13F.

Figure 12G:
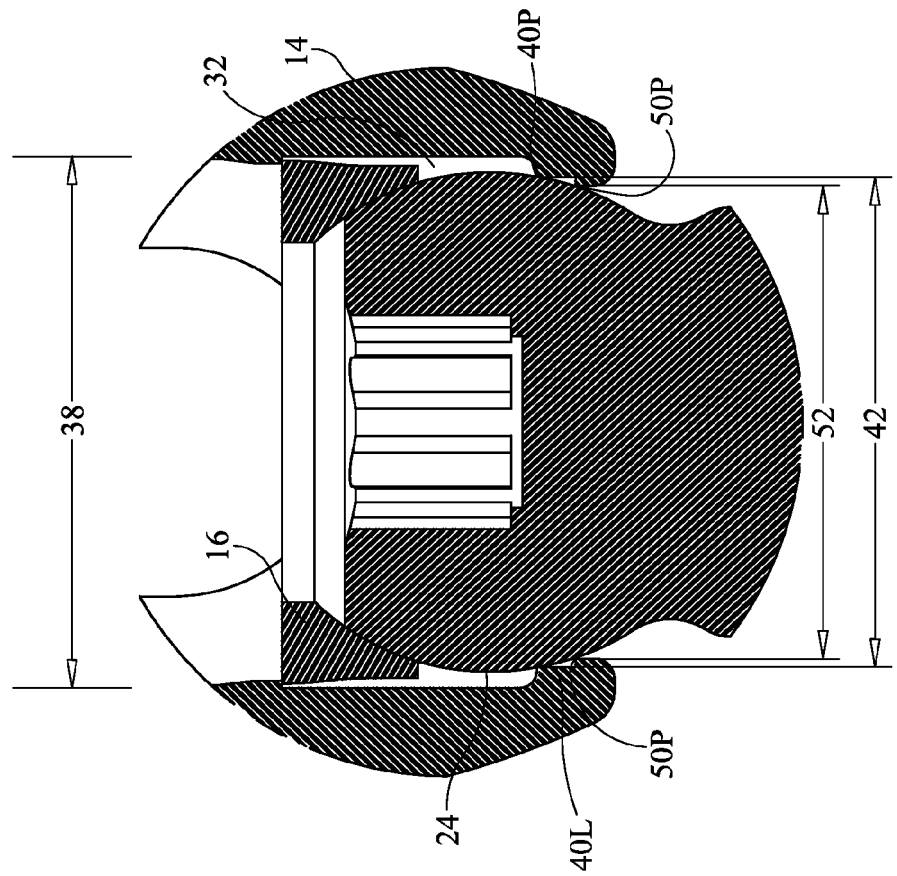
FIG. 12G is an enlarged detailed view of the portion of FIG. 12F within circle 12G.
Figure 12F:
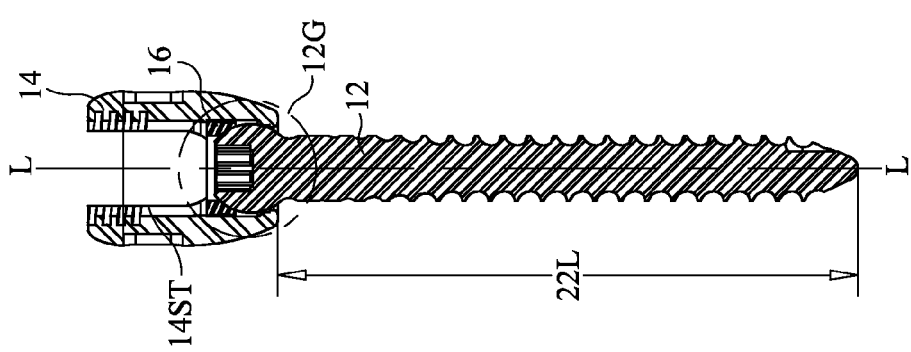
FIG. 12F is a longitudinal sectional view of the assembly of FIG. 12A, similar to that shown in FIG. 12B, but when the assembly is in a locked configuration.

FIG. 12F is a longitudinal sectional view of the assembly 10, similar to that shown in FIG. 12B, but when the assembly 10 is in a locked configuration. FIG. 12G is an enlarged detailed view of the portion of FIG. 12F within circle 12G. When in a locked configuration the external surface of the head 24 contacts both first step feature 40 and second step feature 50. To establish a locked configuration, a compression force is established between head 24 and step features 40, 50. This is typically accomplished by applying force in a distal direction to the proximal end of head 24 while holding tulip 14 relatively stationary, applying force to tulip 14 in a proximal direction while holding head 24 relatively stationary, or most typically, applying force to head 24 in a distal direction while drawing tulip 14 in a proximal direction. Upon application of sufficient force (typically in the range of about 4.0 Nm to about 7.0 Nm, more typically in the range of about 5.0 Nm to 6.0 Nm, although the preferred force may vary depending upon the dimensions of the components, the materials from which they are made, and whether provisional or final locking is intended, for example) the external surface of the head 24 and step features 40, 50 engage one another such that at least one of a portion of the external surface of the head 24 contacting the step feature 40 and step feature 40 partially deforms and typically a slight cold welding results, while at least frictional contact is established between the external surface of the head 24 and step feature 50, resulting in provisional locking. Upon application of more force (typically in the range of about 7.5 Nm to about 12.5 Nm, more typically in the range of about 9.5 Nm to about 10.5 Nm). at least one of a portion of the external surface of the head 24 contacting step feature 50 and step feature 50 also deform and establish additional (further augmented) cold welding and final locking. This results in final locking of head 24 relative to tulip 14, thereby preventing movements of head 24 relative to tulip 14.

It is possible, if necessary to unlock the assembly 10 after a provisional or final locking condition has been established. This can be accomplished by removal of the compression force, after which a tool can be inserted into bore 32 to pry tulip 14 free from head 24, thereby breaking the cold welds, or by any other technique that breaks the cold welds, such as by proximal movement of head 24 relative to tulip 14 or distal movement of tulip 14 relative to head 24.

Figure 12J:
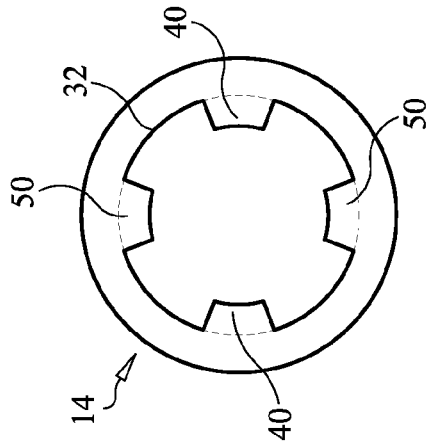
FIGS. 12H-12L illustrate various arrangements of first and second step features according to embodiments of the present invention.
Figure 12I:
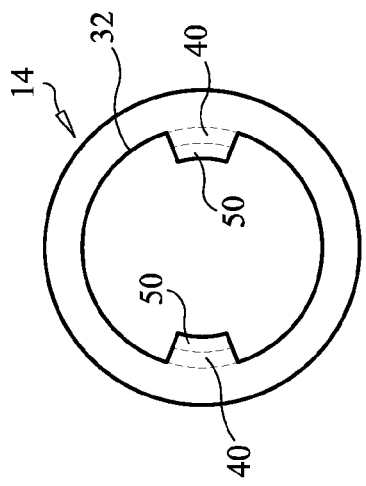
Figure 12H:
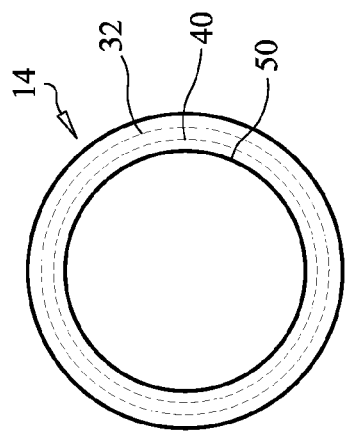
Figure 12L:
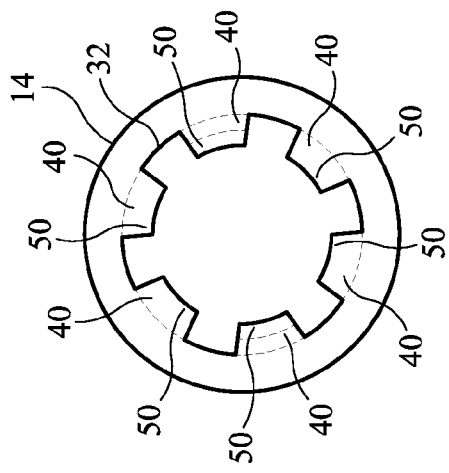
Figure 12K:
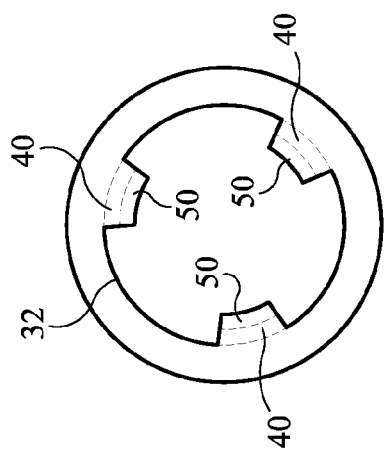

Preferably step features 40 and 50 extend continuously about the entire inner circumference of bore 32 as illustrated in the schematic distal end view of tulip 14. Alternatively, step features 40 and 50 may be discontinuously provided in various arrangements. FIG. 12I illustrates an arrangement in which a pair of step features 40 and a pair of step features 50 extend from bore 32 and are diametrically opposed with one another, with step features 40 and 50 being aligned with one another in the longitudinal axis direction. FIG. 12J illustrates an arrangement in which a pair of step features 40 and a pair of step features 50 extend from bore 32 and are diametrically opposed with one another, with step features 40 and 50 being offset to one another by ninety degrees. FIG. 12K illustrates an arrangement in which a three step features 40 are equidistantly spaced about the circumference of bore 32 and three step features 50 are equidistantly spaced about the circumference of bore 32, with respective features 40 and 50 being aligned in the longitudinal direction. Alternatively, features 40 may be offset from features 50 when viewed in the direction of the longitudinal axis L-L. FIG. 12L illustrates an arrangement in which a pair of first step features 40 are diametrically opposed and six second step features 50 are equidistantly spaced about the circumference of bore 32. Likewise, an embodiment could be provided with two step features 50 and six step features 40. Further alternatively to continuous step features 40 and 50, any number of discontinuous first step features 40 and any number of discontinuous second step features 50 may be provided, with any circumferential positioning (relative to the circumference of bore 32) desired. Also, the step features 40 may be aligned longitudinally with the step features 50 and/or staggered.

Referring now back to FIGS. 12D and 12G, a preferred configuration of the first and second step features 40,50 is described. A proximal end portion 40P that extends from the bore 32 is the portion of the step feature 40 that contacts the external surface of the head 24 and deforms and/or is deformed by head 24 during locking. Likewise, proximal end portion 50P that extends from the bore 32 is the portion of the step feature 50 that contacts the external surface of the head 24 during locking and, in embodiments where deformation takes place, deforms and/or is deformed by head 24 during locking. A longitudinal surface 40L of first step feature 40 extends distally away from proximal end portion 40P and preferably extends tangentially and distally away from the external surface of head 24 when proximal portion 40P contacts the external surface of the head 24. Alternatively, the longitudinal surface 40L may extend away from the external surface of the head 24 at some other angle, but preferably does not contact the external surface of the head 24 even in the locked configuration. A longitudinal surface 50L of second step feature 50 extends distally away from proximal end portion 50P and preferably extends tangentially and distally away from the external surface of head 24 when proximal portion 50P contacts the external surface of the head 24. Alternatively, the longitudinal surface 50L may extend away from the external surface of the head 24 at some other angle, but preferably does not contact the external surface of the head 24 even in the locked configuration.

Referring to FIGS. 12B, 12C and 12F, the tulip 14 includes a slot extending therethrough normal to the longitudinal axis L-L of bore 32. Slot 14ST is configured and dimensioned to receive a rod, shaft, plate or channel for connection to assembly 10. A saddle 16 is configured and dimensioned to be fitted in the bore 32 of tulip 14 against the head 24 to prevent the head 24 from moving proximally relative to the tulip 14. Saddle 16 is configured and dimensioned to be fixed relative to tulip 14 while abutting the proximal portion of head 24. Saddle 16 has a concave distal surface 16S configured and dimensioned as a bearing surface to allow the convex curvature of head 24 to slide relative thereto. Accordingly, as shaft 22 is pivoted relative to tulip 14, head 24 rotates against bearing surfaces of the tulip 14/bore 32 and saddle 16. The limits of pivoting are established by the shaft 22 contacting against the tulip 14. Threading 14X in tulip 14 allows a set screw 46 (see FIG. 10) or other driving member to be torqued or otherwise driven against the rod, shaft, plate or channel to fix it relative to the tulip 14, and also to apply force to the saddle 16, which in turn drives compression of the head 24 relative to the step features 40, 50 to established a locked configuration. Thus, the saddle 16 is configured to apply compression to the head 24 to lock an orientation of the fastener 12 relative to the tulip 14, by driving the external surface of the head 24 against the first and second step features 40, 50.

All components 12,14, 16, 40 and 50 of assembly 10 are preferably made of titanium. One or more components may be made of an alternative material such as cobalt chromium alloys, stainless steel, or any of the other alternative materials described above. The step features 40 and 50 are preferably integrally made with the tulip 14, such as by machining, metal sintering, direct metal deposition or casting. Alternatively, the step features 40, 50 can be integrally attached to the tulip to extend from the bore 32 in the manners described, by welding, or some other permanent attachment method that will not release even when the proximal portions of the step features 40, 50 are plastically deformed under the compression forces. The dimensions of the components will vary depending upon the location of the spine (or elsewhere in the body) in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length 22L of shaft 22 typically falls within a range of about 8 mm to about 100 mm. The inside diameter 38 of bore 32 is typically within the range of about 3 mm to about 11.5 mm. The inside diameter 38 in the embodiment shown in FIG. 12D is about 8.1 mm and the inside diameter 38 in the embodiment shown in FIG. 12G is about 9.6 mm. The outside diameter of head 24 is typically within the range of about 2.5 mm to about 11.5 mm. The outside diameter of head 24 in the embodiment shown in FIG. 12D is about 7.5 mm and the outside diameter of head 24 in the embodiment shown in FIG. 12G is about 9 mm. Dimension 52 is typically in the range of about 2 mm to about 11 mm, more typically in the range of about 6 mm to about 9 mm. In one preferred embodiment, dimension 52 was about 7.05 mm. In another preferred embodiment, dimension 52 was about 8.55 mm. Dimension 42 is typically in the range of about 2.3 mm to about 11.3 mm, more typically in the range of about 6.3 mm to about 9.3 mm. However, the dimensions 42 and 52 may vary from these ranges, as dimensions of 38 and the outside diameter of head 24 vary. In one preferred embodiment, where dimension 52 was about 7.05 mm, dimension 42 was about 7.35 mm. In another preferred embodiment, where dimension 52 was about 8.55 mm, dimension 42 was about 8.85 mm. The tolerance between head 24 and bore 32 is typically in the range of about 0.3 mm to about 0.9 mm. The tolerance in the embodiments of FIGS. 12D and 12G is about 0.6 mm±0.05 mm.

FIGS. 13A-13E illustrate a fastener 10 with extended reduction tabs 14T according to an embodiment of the present invention. FIGS. 13A-13E depict a fastener 10 of the type shown in FIGS. 12A-12E, except that the tulip 14 and channel 32 have been extended by reduction tabs 14T that extend proximally from the proximal end of tulip 14 as it is shown in FIG. 12A. It is noted that extended reduction tabs 14T are not limited to modification of the embodiment of FIGS. 12A-12E, but can be likewise provided on any of the embodiments described herein, as well as on any tulip of any monoaxial, uniplanar, multi-planar or polyaxial fastener.

FIG. 13A is a plan view of the surgical screw assembly 10 with reduction tabs 14T. In the embodiment of FIG. 13A, the surgical screw assembly is a polyaxial surgical screw assembly, meaning that, in an unlocked condition, shaft 22 can pivot relative to tulip 14 in any plane. However, the locking force augmentation features (e.g., the step features, arrangement and functioning of the tulip and head, and methods of providing enhanced locking force) as described with this embodiment are equally applicable to uniplanar surgical screw assemblies, such as those described above, as well as screw assemblies that can pivot in multiple planes but not all planes, and generally to all polyaxial and uniplanar screw assemblies to provide enhanced locking force.

Reduction tabs 14T are integrally provided to extend from the main body of tulip 14. Alternatively, reduction tabs 14T can be joined to tulip 14 by welding or other equivalent attachment means, provided that the reduction tabs 14T can be readily separated from the main body tulip 14, such as by breaking them off. In the embodiment shown in FIG. 13A, reduction tabs 14T are formed integrally with tulip 14 by machining, metal sintering, direct metal deposition, casting or the like. A weakened section such as neck region 14N is provided at the junction of each reduction tab 14T with the main body of the tulip 14, to facilitate readily breaking off the reduction tabs 14T from tulip 14 thereby separating them. A reduction fastener 10 is used in situations such as when a vertebra has been pushed forward (anteriorly slipped) such that it resides at a lower level than the rest of the vertebrae when the patient is lying on his/her stomach. In these situations, a fastener 10 without reduction tabs 14T, when installed into such a vertebra, becomes oriented such that the rod 150 cannot reach the slot 14ST to be received therein so that the driver 46 can be installed into the slot 14ST and driven against the rod 150 to draw up the vertebra. To remedy this, extended reduction tab fastener 10 includes reduction tabs 14T that extend the slot 14EST so that the slot reaches the rod 150, and allows rod 150 to be received therein sufficiently to install driver 46 on top of rod 150 to be driven against the rod 150 and draw up the vertebra.

FIG. 13B is a longitudinal sectional view of the assembly 10 taken along line 13B-13B in FIG. 13A. FIG. 13C is a perspective view of the assembly 10 of FIG. 13A. FIGS. 13B-C illustrate that there are two reduction tabs 14T, one on each side of slot 14EST. Of course, some other number of reduction tabs 14T could be provided, so long as they adequately function to extend the slot 14EST, to draw up the vertebra as described, and are readily removable. In the embodiment shown in FIG. 13B, reduction tabs 14T extend the slot 14ST to form extended slot 14EST which is more than twice as long as slot 14ST of FIG. 12A or the slot formed solely by the main body of the tulip 14 in FIG. 13B. Reduction tabs 14T typically have a length in the range of about 10 mm to about 200 mm, more typically within the range of about 15 mm to about 125 mm. Reduction tabs 14T are provided with threading 14X that cooperates continuously with the threading 14X in the slot 14ST of the main body of the tulip 14. In this way, driver 46 can be seamlessly threaded through the reduction tabs 14T and into the main body of the tulip 14, as the vertebra is drawn up and the main body of the tulip 14 is drawn over the rod 150 such that rod 150 is received in the slot 14ST of the main body of the tulip 14. Once this has been accomplished, the reduction tabs 14T can be broken off from the tulip and removed from the surgical site.

The assembly 10 of the embodiment of FIGS. 13A-13E includes a fastener 12 including an elongate shaft 22 and a head 24 at a proximal end of the shaft 22. As shown, elongate shaft 22 is a screw shaft having threads 26 therealong. Head 24 is substantially spherical, having a convex external surface. A tulip 14 has a bore 32 therethrough that defines a bearing surface against which head 24 can rotate when assembly 10 is in an unlocked configuration. Bore 32 is dimensioned to allow the distal end of elongate shaft 12 to pass therethrough as well as to allow the head 24 to be inserted into the tulip 14.

FIG. 13D is an enlarged detailed view of the portion of FIG. 13B within circle 13D. A first step feature 40 is located at a distal end portion of bore 32 and extends inwardly therefrom. The first step feature 40 reduces the diameter 38 of bore 32 to a dimension 42 that allows the distal end of the elongate shaft to pass therethrough, and allows all of the shaft 22 to pass therethrough, but prevents passage of head 24 therethrough as a portion of the first step feature contacts the external surface of the head, as shown in FIG. 13D. A second step feature 50 is located at a distal end portion of bore 32, distally of first step feature 40. Second step feature 50 further reduces the diameter of bore 32 to a dimension 52 less than dimension 42 established by first step feature 40, the further reduced dimension 52 allowing the distal end of the elongate shaft 22 to pass therethrough, and allows all of the shaft 22 to pass therethrough, but prevents passage of head 24 therethrough.

FIG. 13E is a top view of the assembly 10 of FIG. 13A. A tool interface 16T is provided in the proximal end of head 24 that can be interfaced by a tool to drive the fastener 12 into the bone. The present invention is not limited to this type of interface as any other equivalent type of torqueing interface could be used.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A surgical screw assembly comprising:
   a fastener including an elongate shaft having a proximal end and a distal end and a head at said proximal end, said head having an external surface;
   a tulip having a tulip proximal end, a tulip distal end, an external surface and an internal bearing surface, said tulip distal end having a bore therethrough defining said internal bearing surface and having a diameter dimensioned to allow said distal end of said elongate shaft to pass therethrough;
   a first step feature located at a distal end portion of said bore and extending inwardly from said bore, said first step feature reducing the diameter of said bore to allow said distal end of said elongate shaft to pass therethrough, but prevent passage of said head therethrough as a portion of said first step feature contacts said external surface of said head; and
   a second step feature located at a distal end portion of said bore, distally of said first step feature, said second step feature further reducing the diameter of said bore to a dimension less than a dimension established by said first step feature, the further reduced dimension allowing said distal end of said elongate shaft to pass therethrough, but preventing passage of said head therethrough as a portion of said second step feature contacts said external surface of said head and a portion of said first step feature a portion of said first step feature contacts said external surface of said head, wherein, in an unlocked configuration, said external surface of said head contacts said first step feature but does not contact said second step feature.

2. The assembly of claim 1, wherein, in a locked configuration, said external surface of said head contacts said first step feature and said second step feature.

3. The assembly of claim 1, wherein said first step feature extends from at least two locations of said bore equally positioned relative to each other relative to a longitudinal axis of said bore, and said second step feature extends from at least two locations of said bore distal of said locations from which said first step feature extends and equally positioned relative to each other relative to said longitudinal axis of said bore.

4. The assembly of claim 3, wherein said at least two locations from which said first step feature extends are diametrically opposite one another, relative to a circumference of said bore and said at least two locations from which said second step feature extends are diametrically opposite one another, relative to said circumference of said bore.

5. The assembly of claim 4, wherein said first step feature extends continuously about said circumference of said bore and said second feature extends continuously about said circumference of said bore.

6. The assembly of claim 1, wherein, in a locked configuration, a proximal end portion of said first step feature contacts said external surface of said head and a proximal end portion of said second step feature contacts said head.

7. The assembly of claim 6, wherein a longitudinal surface of said first step feature extends distally away from said proximal end portion of said first step feature contacting said external surface of said head and extends tangentially and distally away from said external surface of said head; and wherein a longitudinal surface of said second step feature extends distally away from said proximal end portion of said second step feature contacting said external surface of said head and extends tangentially and distally away from said external surface of said head.

8. The assembly of claim 1, wherein said first and second step feature portions engage said external surface of said head and lock said head, preventing movements of said head relative to said tulip when a compression force is applied to drive said external surface of said head and said first and second step features against one another under compression.

9. The assembly of claim 8, wherein, upon removal of said compression force, said head is unlockable from said step features upon application of force to at least one of said tulip and said head.

10. The assembly of claim 1, wherein said tulip further comprises a slot extending therethrough normal to a longitudinal axis of said bore, said slot configured and dimensioned to receive a rod, plate, shaft or channel for connection to said assembly.

11. The assembly of claim 10, further comprising reduction tabs extending proximally of said tulip and extending said slot.

12. The assembly of claim 1, further comprising a saddle, said saddle being configured and dimensioned to be fitted in said tulip against said head of said fastener to prevent said head from moving proximally relative to said tulip.

13. The assembly of claim 12, wherein said saddle is configured to apply compression to said head to lock an orientation of said fastener relative to said tulip, by driving said external surface of said head against said first and second step features.

14. The assembly of claim 13, further comprising a driving member configured to engage a proximal end portion of said tulip and to establish a driving force against a rod, shaft, plate or channel extending through a slot in said tulip.

15. The assembly of claim 14, wherein said driving force also drives said rod, shaft, plate or channel against said saddle and drives said saddle to apply said head against said first and second step features, thereby locking said head relative to said tulip.

16. A method of locking a surgical screw assembly, said method comprising:
   providing an assembly comprising: a fastener including an elongate shaft having a proximal end and a distal end and a head at said proximal end, said head having an external surface; a tulip having a tulip proximal end, a tulip distal end, an external surface and an internal bearing surface, said tulip distal end having a bore therethrough defining said internal bearing surface and having a diameter dimensioned to allow said distal end of said elongate shaft to pass therethrough; a first step feature located at a distal end portion of said bore and extending inwardly from said bore, said first step feature reducing the diameter of said bore to allow said distal end of said elongate shaft to pass therethrough, but prevent passage of said head therethrough as a portion of said first step feature contacts said external surface of said head; and a second step feature located at a distal end portion of said bore, distally of said first step feature, said second step feature further reducing the diameter of said bore to a dimension less than a dimension established by said first step feature, the further reduced diameter allowing said distal end of said elongate shaft to pass therethrough, but preventing passage of said head therethrough; wherein said assembly is provided in an unlocked configuration whereby said head can rotate relative to said tulip; and applying force to said head to drive said head and said step features under compression, thereby locking said assembly such that said head cannot rotate relative to thereby locking said assembly such that said head cannot rotate relative to said tulip, wherein, when in said unlocked configuration, said external surface of said head contacts said first step feature but does not contact said second step feature.

17. The method of claim 16, wherein at least a portion of at least one of said external surface of said head and said first step feature deforms as a result of said applying force.

18. The method of claim 17, wherein at least a portion of at least one of said external surface of said head and said second step feature deforms as a result of said applying force.

* * * * *

UNITED STATES PATENT AND TRADEMARK OFFICE
CERTIFICATE OF CORRECTION

PATENT NO.         : 9,034,022 B2
APPLICATION NO.    : 13/717565
DATED              : May 19, 2015
INVENTOR(S)        : Asaad et al.

Page 1 of 1

It is certified that error appears in the above-identified patent and that said Letters Patent is hereby corrected as shown below:

In the specification

Column 1, line 54, please delete "vertebrae o" and insert --vertebrae to--.

Signed and Sealed this
Third Day of May, 2016

Michelle K. Lee
*Director of the United States Patent and Trademark Office*